(12) United States Patent
Nguyen et al.

(10) Patent No.: US 8,653,062 B2
(45) Date of Patent: Feb. 18, 2014

(54) COMPOUNDS AS RECEPTOR MODULATORS WITH THERAPEUTIC UTILITY

(75) Inventors: Phong X. Nguyen, Placentia, CA (US); Todd M. Heidelbaugh, Fountain Valley, CA (US)

(73) Assignee: Allergan, Inc., Irvine, CA (US)

( * ) Notice: Subject to any disclaimer, the term of this patent is extended or adjusted under 35 U.S.C. 154(b) by 421 days.

(21) Appl. No.: 12/951,317

(22) Filed: Nov. 22, 2010

(65) Prior Publication Data
US 2011/0152241 A1 Jun. 23, 2011

Related U.S. Application Data

(60) Provisional application No. 61/264,038, filed on Nov. 24, 2009.

(51) Int. Cl.
| | | |
|---|---|---|
| *A61K 31/397* | (2006.01) | |
| *A61K 31/421* | (2006.01) | |
| *A61K 31/4155* | (2006.01) | |
| *A61K 31/426* | (2006.01) | |
| *A61K 31/427* | (2006.01) | |
| *C07D 401/12* | (2006.01) | |
| *C07D 403/12* | (2006.01) | |
| *C07D 405/12* | (2006.01) | |
| *C07D 417/12* | (2006.01) | |
| *C07D 333/06* | (2006.01) | |

(52) U.S. Cl.
USPC .......... 514/210.17; 514/210.18; 514/365; 514/374; 514/444; 514/340; 548/953; 548/201; 548/364.1; 548/236; 548/406; 546/268.1; 549/71

(58) Field of Classification Search
None
See application file for complete search history.

(56) References Cited

U.S. PATENT DOCUMENTS

| | | | |
|---|---|---|---|
| 4,952,683 A | 8/1990 | Tschannen et al. | |
| 5,102,901 A | 4/1992 | van Wijngaarden et al. | |
| 5,110,987 A | 5/1992 | Liotta et al. | |
| 5,294,722 A | 3/1994 | Kim | |
| 5,403,851 A | 4/1995 | D'Orlando et al. | |
| 5,580,878 A | 12/1996 | D'Orlando et al. | |
| 6,235,912 B1 | 5/2001 | Takesako et al. | |
| 6,239,297 B1 | 5/2001 | Takesako et al. | |
| 2003/0125371 A1 | 7/2003 | Elokdah | |
| 2009/0312315 A1 | 12/2009 | Yamaguchi | |

FOREIGN PATENT DOCUMENTS

| | | |
|---|---|---|
| WO | WO 03/061567 | 7/2003 |
| WO | WO 03/062248 | 7/2003 |
| WO | WO 2008/030838 | 3/2008 |
| WO | WO 2008/030843 | 3/2008 |

OTHER PUBLICATIONS

Hale Jeffrey J et al: "A Rational Utilization of High-Throughput Screening Affords Selective, Orally Bioavailable 1-Benzyl-3-carboxyazetidine Sphingosine-1- phosphate -1 Receptor Agonlsts", Journal of Medicinal Chemistry, American Chemical Society; vol. 47, No. 27, Jan. 1, 2004.

Yifeng Xiong; "Discovery and Structure-Activity Relationship of 3-Methoxy-N-(3-(1-methyl-1H-pyrazol-5-yl)-4-(2-morpholinoethoxy)phenyl)benzamide (APD791): A Highly Selective 5-Hydroxytryptamine2A Receptor Inverse Agonist for the Treatment of Arterial Thrombosis"; Journal of Medicinal Chemistry 2010, 53, 4412-4421.

Peter Dosa; "Solubilized phenyl-pyrazole ureas as potent, selective 5-HT2A inverse-agonists and their application as antiplatelet agents"; Bioorganic & Medicinal Chemistry Letters 19 (2009) 5486-5489.

Cross, L.C. et al, Rules for the Nomenclature of Organic Chemistry, Section E: Stereochemistry, Pure & Appl. Chem., 1976, 11-30, 45.

Muller, Inorganic Structural Chemistry, Apr. 15, 1993, pp. 14-15.

Saag et al., Teriparatide or Alendronate in Glucocorticoid-Induced Osteoporosis, The New England Journal of Medicine, 2007, 357:2028-39.

Stahl, Heinrich et al, Handbook of Pharmaceutical Salts, Verlag Helvetica Chimica Acta—Zurich, 2002, 329-345.

Vippagunta, Sudha et al, Crystalline Solids, Advanced Drug Delivery Reviews, 2001, 3-26, 48.

*Primary Examiner* — Michael Barker
(74) *Attorney, Agent, or Firm* — Doina G. Ene

(57) ABSTRACT

The present invention relates to novel cyclic amine and cycloalkyl derivatives, processes for preparing them, pharmaceutical compositions containing them and their use as pharmaceuticals as modulators of sphingosine-1-phosphate receptors.

16 Claims, 1 Drawing Sheet

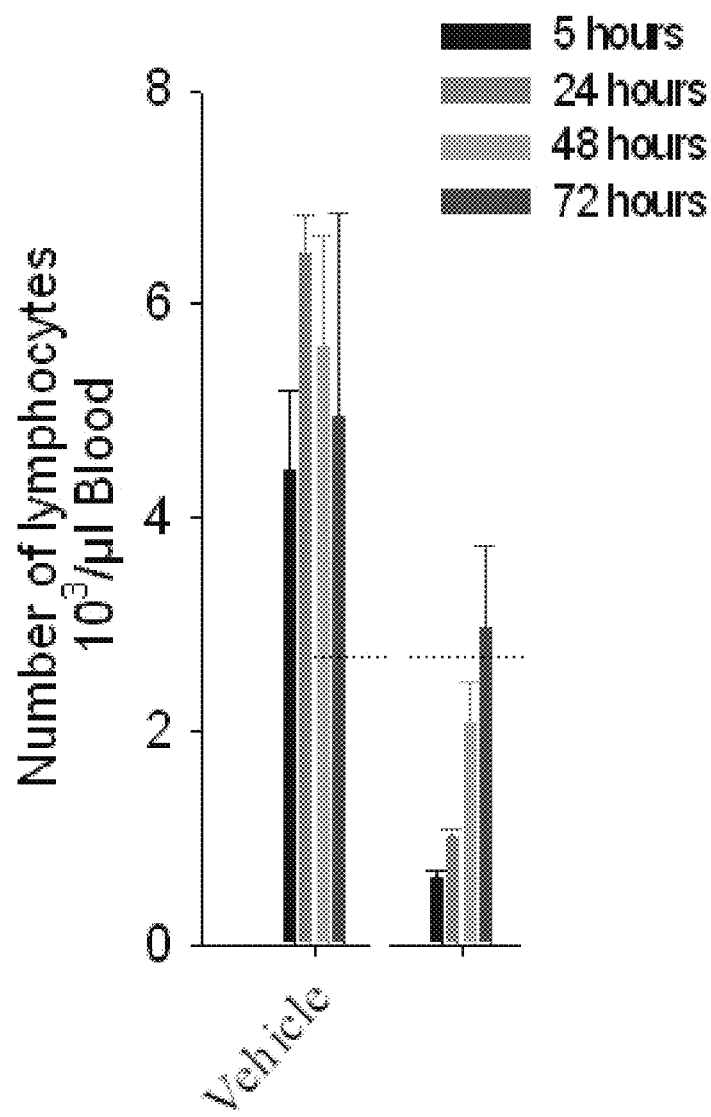
Lymphopenia induced by S1P1 agonists in mice: Time course (10 mg/Kg ip)
1-{4-[(5-phenylpentyl)oxy]-3-(2-thienyl)benzyl}azetidine-3-carboxylic acid

COMPOUNDS AS RECEPTOR MODULATORS WITH THERAPEUTIC UTILITY

CROSS REFERENCE TO RELATED APPLICATIONS

This application claims the benefit of U.S. Provisional Application Ser. No. 61/264,038 filed on Nov. 24, 2009, which is hereby incorporated by reference in its entirety.

FIELD OF THE INVENTION

The present invention relates to novel cyclic amine and cycloalkyl derivatives, processes for preparing them, pharmaceutical compositions containing them and their use as pharmaceuticals as modulators of sphingosine-1-phosphate receptors. The invention relates specifically to the use of these compounds and their pharmaceutical compositions to treat disorders associated with sphingosine-1-phosphate (S1P) receptor modulation.

BACKGROUND OF THE INVENTION

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

SUMMARY OF THE INVENTION

We have now discovered a group of novel compounds which are potent and selective sphingosine-1-phosphate modulators. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This invention describes compounds of Formula I, which have sphingosine-1-phosphate receptor biological activity. The compounds in accordance with the present invention are thus of use in medicine, for example in the treatment of humans with diseases and conditions that are alleviated by S1P modulation. In one aspect, the invention provides a compound having Formula I or a pharmaceutically acceptable salt thereof or stereoisomeric forms thereof, or the geometrical isomers, enantiomers, diastereoisomers, tautomers, zwitterions and pharmaceutically acceptable salts thereof:

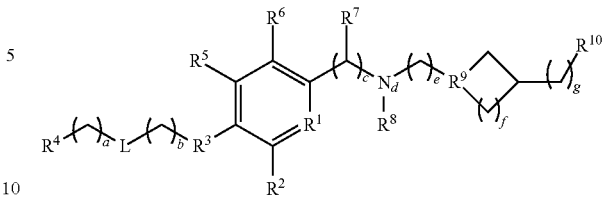

Formula I wherein:
$R^1$ is N or C—$R^{11}$;
$R^2$ is aromatic heterocycle, non-aromatic heterocycle, cycloalkyl, cycloalkenyl or aryl;
$R^3$ is O, N—$R^{12}$, CH—$R^{13}$, S, —$CR^{14}$=$CR^{15}$—, —C≡C— or —C(O)—;
$R^4$ is H, aromatic heterocycle, non-aromatic heterocycle, cycloalkenyl, cycloalkyl or aryl;
$R^5$ is H, halogen, —$OC_{1-3}$ alkyl, $C_{1-3}$ alkyl or hydroxyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H or $C_{1-6}$ alkyl;
$R^9$ is CH or N;
$R^{10}$ is $OPO_3H_2$, carboxylic acid, $PO_3H_2$, $C_{1-6}$ alkyl, —$S(O)_2OH$, —$P(O)MeOH$, —$P(O)(H)OH$ or $OR^{16}$;
$R^{11}$ is H, $C_{1-6}$ alkyl, halogen, hydroxyl or —$OC_{1-3}$ alkyl;
$R^{12}$ is H or $C_{1-3}$ alkyl;
$R^{13}$ is H, $C_{1-3}$ alkyl, halogen, hydroxyl, —$OC_{1-3}$ alkyl or amino;
$R^{14}$ is H or $C_{1-3}$ alkyl;
$R^{15}$ is H or $C_{1-3}$ alkyl;
$R^{16}$ is H or $C_{1-6}$ alkyl;
a is 0, 1, 2, 3 or 4;
b is 0, 1, 2, 3 or 4;
c is 0 or 1;
d is 0 or 1;
e is 0, 1, 2 or 3;
f is 0, 1, 2 or 3;
g is 0, 1, 2 or 3;
L is $CHR^{17}$, O, S, $NR^{18}$ or —C(O)—;
$R^{17}$ is H, $C_{1-3}$ alkyl, —$OC_{1-3}$ alkyl, halogen, hydroxyl or amino; and
$R^{18}$ is H or $C_{1-3}$ alkyl;
with the proviso that when $R^3$ is O, N—$R^{12}$, or S, and b is 0 or 1 then L is not O, S, $NR^{18}$.

The term "alkyl", as used herein, refers to saturated, monovalent or divalent hydrocarbon moieties having linear or branched moieties or combinations thereof and containing 1 to 6 carbon atoms. One methylene (—$CH_2$—) group, of the alkyl can be replaced by oxygen, sulfur, sulfoxide, nitrogen, carbonyl, carboxyl, sulfonyl, or by a divalent $C_{3-6}$ cycloalkyl. Alkyl groups can be substituted by halogen, hydroxyl, cycloalkyl, amino, non-aromatic heterocycles, carboxylic acid, phosphonic acid groups, sulphonic acid groups, phosphoric acid.

The term "cycloalkyl", as used herein, refers to a monovalent or divalent group of 3 to 8 carbon atoms, preferably 3 to 5 carbon atoms derived from a saturated cyclic hydrocarbon. Cycloalkyl groups can be monocyclic or polycyclic. Cycloalkyl can be substituted by 1 to 3 $C_{1-3}$ alkyl groups or 1 or 2 halogens. Usually, in the present case, cycloalkyl group is cyclopentane.

The term "cycloalkenyl", as used herein, refers to a monovalent or divalent group of 3 to 8 carbon atoms, preferably 3 to 6 carbon atoms derived from a saturated cycloalkyl having one double bond. Cycloalkenyl groups can be monocyclic or polycyclic. Cycloalkenyl groups can be substituted by 1 to 3 $C_{1-3}$ alkyl groups or 1 or 2 halogens. Usually, in the present case, cycloalkenyl group is cyclopentene.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. $C_{2-6}$ alkenyl can be in the E or Z configuration. Alkenyl groups can be substituted by 1 to 2 $C_{1-3}$ alkyl.

The term "alkynyl", as used herein, refers to a monovalent or divalent hydrocarbon radical having 2 to 6 carbon atoms, derived from a saturated alkyl, having at least one triple bond.

The term "heterocycle" as used herein, refers to a 3 to 10 membered ring, which can be aromatic or non-aromatic, saturated or non-saturated, containing at least one heteroatom selected form O or N or S or combinations of at least two thereof, interrupting the carbocyclic ring structure. The heterocyclic ring can be saturated or non-saturated. The heterocyclic ring can be interrupted by a C=O; the S heteroatom can be oxidized. Heterocycles can be monocyclic or polycyclic. Heterocyclic ring moieties can be substituted by hydroxyl, 1 to 2 $C_{1-3}$ alkyl or 1 to 2 halogens. Usually, in the present case, heterocyclic groups are 5 or 6 membered rings. Usually, in the present case, heterocyclic groups are pyridine, azetidine, pyrazolidine, pyrroline, pyrrolidine, imidazoline, pyrazoline, thiazoline, oxazoline, thiophene, dihydrothiophene, furan, dihydrofuran, pyrrole, pyrroline, pyrrolidine, oxazole, oxazoline, thiazole, imidazole, pyrazole, pyrazoline, isoxazole, isothiazole, tetrazole, oxadiazole, 1,2,5-oxadiazole, thiadiazole, 1,2,3-triazole, 1,2,4-triazole, imidazole, imidazoline, pyrrolidinone, pyrrol-2(3H)-one, imidazolidin-2-one, or 1,2,4-triazol-5(4H)-one.

The term "aryl" as used herein, refers to an organic moiety derived from an aromatic hydrocarbon consisting of a ring containing 6 to 10 carbon atoms by removal of one hydrogen, which can be substituted by 1 to 3 halogen atoms or by 1 to 2 $C_{1-3}$ alkyl groups. Usually aryl is phenyl.

The group of formula "—$CR^{14}$=$CR^{15}$—", as used herein, represents an alkenyl radical.

The group of formula "—C≡C—", as used herein, represents an alkynyl radical.

The term "hydroxyl" as used herein, represents a group of formula "—OH".

The term "carbonyl" as used herein, represents a group of formula "—C(O)".

The term "carboxyl" as used herein, represents a group of formula "—C(O)O—".

The term "sulfonyl" as used herein, represents a group of formula "—$SO_2$".

The term "sulfate" as used herein, represents a group of formula "—O—S(O)$_2$—O—".

The term "carboxylic acid" as used herein, represents a group of formula "—C(O)OH".

The term "sulfoxide" as used herein, represents a group of formula "—S=O".

The term "phosphonic acid" as used herein, represents a group of formula "—P(O)(OH)$_2$".

The term "phosphoric acid" as used herein, represents a group of formula "—(O)P(O)(OH)$_2$".

The term "boronic acid", as used herein, represents a group of formula "—B(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Generally $R^1$ is N or C—$R^{11}$. Usually, in the present case, $R^1$ is C—$R^{11}$.

Generally $R^2$ is aromatic heterocycle, non-aromatic heterocycle, cycloalkyl, cycloalkenyl or aryl. Usually, in the present case, $R^2$ is aromatic heterocycle, cycloalkyl, cycloalkenyl or aryl. Preferred $R^2$ groups are cyclopentane, cyclopentene, pyrazolidine, pyrroline, pyrrolidine, imidazoline, pyrazoline, thiazoline, oxazoline, thiophene, dihydrothiophene, furan, dihydrofuran, pyrrole, pyrroline, pyrrolidine, oxazole, oxazoline, thiazole, imidazole, pyrazole, pyrazoline, isoxazole, isothiazole, tetrazole, oxadiazole, 1,2,5-oxadiazole, thiadiazole, 1,2,3-triazole, 1,2,4-triazole, imidazole, imidazoline, pyrrolidinone, pyrrol-2(3H)-one, imidazolidin-2-one, or 1,2,4-triazol-5(4H)-one.

Generally $R^3$ is O, N—$R^{12}$, CH—$R^{13}$ or S; —$CR^{14}$=$CR^{15}$—; —C≡C—. Usually, in the present case, $R^3$ is O or S.

Generally $R^4$ is aromatic heterocycle, non-aromatic heterocycle, cycloalkenyl, cycloalkyl or aryl. Usually, in the present case, $R^4$ is aryl.

Generally $R^5$ is H, halogen, —$OC_{1-3}$ alkyl or $C_{1-6}$ alky. Usually, in the present case, $R^5$ is H, halogen or —$OC_{1-3}$ alkyl.

Generally $R^6$ is H, $C_{1-3}$ alkyl, halogen, hydroxyl or —$OC_{1-3}$ alkyl. Usually, in the present case, $R^6$ is H.

Generally $R^7$ is H or $C_{1-6}$ alkyl.

Generally $R^8$ is H or $C_{1-6}$ alkyl. Usually, in the present case, $R^8$ is H.

Generally $R^9$ is CH or N.

Generally $R^{10}$ is $OPO_3H_2$, COOH, $PO_3H_2$, $C_{1-6}$ alkyl, —S(O)$_2$OH, —P(O)MeOH, —P(O)(H)OH or $OR^{16}$. Usually, in the present case, $R^{10}$ is COOH.

Generally $R^{11}$ is H, $C_{1-3}$ alkyl, halogen, hydroxyl or —$OC_{1-3}$ alkyl. Usually, in the present case, $R^{11}$ is H.

Generally $R^{12}$ is H or $C_{1-3}$ alkyl

Generally $R^{13}$ is H, $C_{1-3}$ alkyl, halogen, hydroxyl, —$OC_{1-3}$ alkyl or amino.

Generally $R^{14}$ is H or $C_{1-3}$ alkyl.

Generally $R^{15}$ is H or $C_{1-3}$ alkyl.

Generally $R^{16}$ is H or $C_{1-6}$ alkyl.

Generally a is 0, 1, 2, 3 or 4. Usually, in the present case, a is 0, 1, 2, or 3.

Generally b is 0, 1, 2, 3 or 4. Usually, in the present case, b is 1, 2, or 3.

Generally c is 0 or 1.

Generally d is 0 or 1. Usually, in the present case, d is 0 or 1.

Generally e is 0 to 3. Usually, in the present case, e is 0 or 1.

Generally f is 0 to 3. Usually, in the present case, f is 1.

Generally g is 0 to 3. Usually g is 0.

Generally L is $CHR^{17}$, O, S, —C(O) or $NR^{18}$. Usually, in the present case, L is $CHR^{17}$ or O.

Generally $R^{17}$ is H, $C_{1-3}$ alkyl, —$OC_{1-3}$ alkyl, halogen, hydroxyl or amino. Usually, in the present case, $R^{17}$ is H or $C_{1-3}$ alkyl.

Generally $R^{18}$ is H or $C_{1-3}$ alkyl.

In one embodiment of the invention $R^1$ is N or C—$R^{11}$;

$R^2$ is a 5-member aromatic heterocycle, or 5-member cycloalkenyl;

$R^3$ is O, N—$R^{12}$, CH—$R^{13}$, S, —$CR^{14}$=$CR^{15}$—, —C≡C— or —C(O)—;
$R^4$ is H, aromatic heterocycle, non-aromatic heterocycle, cycloalkyl, cycloalkenyl or aryl;
$R^5$ is H, halogen, —$OC_{1-3}$ alkyl, $C_{1-3}$ alkyl or hydroxyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H or $C_{1-6}$ alkyl;
$R^9$ is CH or N;
$R^{10}$ is $OPO_3H_2$, carboxylic acid, —$PO_3H_2$, $C_{1-6}$ alkyl, —$S(O)_2OH$, —P(O)MeOH, —P(O)(H)OH or —$OR^{16}$;
$R^{11}$ is H, $C_{1-6}$ alkyl, halogen, hydroxyl or —$OC_{1-3}$ alkyl;
$R^{12}$ is H or $C_{1-3}$ alkyl;
$R^{13}$ is H, $C_{1-3}$ alkyl, halogen, hydroxyl, —$OC_{1-3}$alkyl or amino;
$R^{14}$ is H or $C_{1-3}$ alkyl;
$R^{15}$ is H or $C_{1-3}$ alkyl;
$R^{16}$ is H or $C_{1-6}$ alkyl;
a is 0, 1, 2, 3 or 4;
b is 0, 1, 2, 3 or 4;
c is 0 or 1;
d is 0 or 1;
e is 0, 1, 2 or 3;
f is 0, 1, 2 or 3;
g is 0, 1, 2 or 3;
L is $CHR^{17}$, O, S, $NR^{18}$ or —C(O)—;
$R^{17}$ is H, $C_{1-3}$ alkyl, —$OC_{1-3}$ alkyl, halogen, hydroxyl or amino, and
$R^{18}$ is H or $C_{1-3}$ alkyl;
with the proviso that when $R^3$ is O, N—$R^{12}$, S and b is 0 or 1 then L is not O, S, $NR^{18}$.

In another embodiment of the invention
$R^1$ is N or C—$R^{11}$;
$R^2$ is a cyclopentane, cyclopentene, pyrazolidine, pyrroline, pyrrolidine, imidazoline, pyrazoline, thiazoline, oxazoline, thiophene, dihydrothiophene, furan, dihydrofuran, pyrrole, pyrroline, pyrrolidine, oxazole, oxazoline, thiazole, imidazole, pyrazole, pyrazoline, isoxazole, isothiazole, tetrazole, oxadiazole, 1,2,5-oxadiazole, thiadiazole, 1,2,3-triazole, 1,2,4-triazole, imidazole, imidazoline, pyrrolidinone, pyrrol-2(3H)-one, imidazolidin-2-one, or 1,2,4-triazol-5(4H)-one;
$R^3$ is O, N—$R^{12}$, CH—$R^{13}$, S, —$CR^{14}$=$CR^{15}$—, —C≡C— or —C(O)—;
$R^4$ is H, aromatic heterocycle, non-aromatic heterocycle, cycloalkyl, cycloalkenyl or aryl;
$R^5$ is H, halogen, —$OC_{1-3}$ alkyl, $C_{1-3}$ alkyl or hydroxyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H or $C_{1-6}$ alkyl;
$R^9$ is CH or N;
$R^{10}$ is $OPO_3H_2$, carboxylic acid, —$PO_3H_2$, $C_{1-6}$ alkyl, —$S(O)_2OH$, —P(O)MeOH, —P(O)(H)OH or —$OR^{16}$;
$R^{11}$ is H, $C_{1-6}$ alkyl, halogen, hydroxyl or —$OC_{1-3}$ alkyl;
$R^{12}$ is H or $C_{1-3}$ alkyl;
$R^{13}$ is H, $C_{1-3}$ alkyl, halogen, hydroxyl, —$OC_{1-3}$alkyl or amino;
$R^{14}$ is H or $C_{1-3}$ alkyl;
$R^{15}$ is H or $C_{1-3}$ alkyl;
$R^{16}$ is H or $C_{1-6}$ alkyl;
a is 0, 1, 2, 3 or 4;
b is 0, 1, 2, 3 or 4;
c is 0 or 1;
d is 0 or 1;
e is 0, 1, 2 or 3;
f is 0, 1, 2 or 3;
g is 0, 1, 2 or 3;
L is $CHR^{17}$, O, S, $NR^{18}$ or —C(O)—;
$R^{17}$ is H, $C_{1-3}$ alkyl, —$OC_{1-3}$ alkyl, halogen, hydroxyl or amino, and
$R^{18}$ is H or $C_{1-3}$ alkyl;
with the proviso that when $R^3$ is O, N—$R^{12}$, S and b is 0 or 1 then L is not O, S, $NR^{18}$.

In another embodiment of the invention
$R^1$ is N;
$R^2$ is aromatic heterocycle, non-aromatic heterocycle, cycloalkyl, cycloalkenyl or aryl;
$R^3$ is O, N—$R^{12}$, CH—$R^{13}$, S, —$CR^{14}$=$CR^{15}$—, —C≡C— or —C(O)—;
$R^4$ is H, aromatic heterocycle, non-aromatic heterocycle, cycloalkyl, cycloalkenyl or aryl;
$R^5$ is H, halogen, —$OC_{1-3}$ alkyl, $C_{1-3}$ alkyl or hydroxyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H or $C_{1-6}$ alkyl;
$R^9$ is CH or N;
$R^{10}$ is $OPO_3H_2$, carboxylic acid, —$PO_3H_2$, $C_{1-6}$ alkyl, —$S(O)_2OH$, —P(O)MeOH, —P(O)(H)OH or —$OR^{16}$;
$R^{12}$ is H or $C_{1-3}$ alkyl;
$R^{13}$ is H, $C_{1-3}$ alkyl, halogen, hydroxyl, —$OC_{1-3}$alkyl or amino;
$R^{14}$ is H or $C_{1-3}$ alkyl;
$R^{15}$ is H or $C_{1-3}$ alkyl;
$R^{16}$ is H or $C_{1-6}$ alkyl;
a is 0, 1, 2, 3 or 4;
b is 0, 1, 2, 3 or 4;
c is 0 or 1;
d is 0 or 1;
e is 0, 1, 2 or 3;
f is 0, 1, 2 or 3;
g is 0, 1, 2 or 3;
L is $CHR^{17}$, O, S, $NR^{18}$ or —C(O)—;
$R^{17}$ is H, $C_{1-3}$ alkyl, —$OC_{1-3}$ alkyl, halogen, hydroxyl or amino, and
$R^{18}$ is H or $C_{1-3}$ alkyl;
with the proviso that when $R^3$ is O, N—$R^{12}$, S and b is 0 or 1 then L is not O, S, $NR^{18}$.

In another embodiment of the invention
$R^1$ is C—$R^{11}$; and
$R^2$ is aromatic heterocycle, non-aromatic heterocycle or cycloalkenyl; and
$R^3$ is O or S; and
$R^4$ is aryl; and
$R^5$ is H, —$OC_{1-3}$ alkyl or halogen; and
$R^6$ is H; and
$R^7$ is H or $C_{1-6}$ alkyl; and
$R^8$ is H; and
$R^9$ is CH or N; and
$R^{10}$ is COOH; and
$R^{11}$ is H; and
a is 0, 1, 2 or 3; and
b is 1, 2 or 3; and
c is 0 or 1; and
d is 0 or 1; and
e is 0 or 1; and
f is 1; and
g is 0; and
L is $CHR^{17}$ or O; and
$R^{17}$ is H or $C_{1-3}$ alkyl;
with the proviso that when $R^3$ is O or S and b is 1 then L is not O.

In another embodiment of the invention
$R^1$ is C—$R^{11}$; and
$R^2$ is aromatic heterocycle, non-aromatic heterocycle or cycloalkenyl; and
$R^3$ is O; and
$R^4$ is aryl; and
$R^5$ is H, —$OC_{1-3}$ alkyl or halogen; and
$R^6$ is H; and
$R^7$ is H or $C_{1-6}$ alkyl; and
$R^8$ is H; and
$R^9$ is CH; and
$R^{10}$ is COOH; and
$R^{11}$ is H; and
a is 0, 1, 2 or 3; and
b is 1, 2 or 3; and
c is 1; and
d is 1; and
e is 0 or 1; and
f is 1; and
g is 0; and
L is $CHR^{17}$; and
$R^{17}$ is H.

In another embodiment of the invention
$R^1$ is C—$R^{11}$; and
$R^2$ is aromatic heterocycle, non-aromatic heterocycle or cycloalkenyl; and
$R^3$ is S; and
$R^4$ is aryl; and
$R^5$ is H, —$OC_{1-3}$ alkyl or halogen; and
$R^6$ is H; and
$R^7$ is H or $C_{1-6}$ alkyl; and
$R^8$ is H; and
$R^9$ is CH or N; and
$R^{10}$ is COOH; and
$R^{11}$ is H; and
a is 0, 1, 2 or 3; and
b is 1, 2 or 3; and
c is 0 or 1; and
d is 0 or 1; and
e is 0 or 1; and
f is 1; and
g is 0; and
L is $CHR^{17}$ or O; and
$R^{17}$ is H or $C_{1-3}$ alkyl;
with the provision that when $R^3$ is S and b is 1 then L is not O.

In another embodiment of the invention
$R^1$ is C—$R^{11}$; and
$R^2$ is aromatic heterocycle, non-aromatic heterocycle or cycloalkenyl; and
$R^3$ is O; and
$R^4$ is aryl; and
$R^5$ is H, —$OC_{1-3}$ alkyl or halogen; and
$R^6$ is H; and
$R^7$ is H or $C_{1-6}$ alkyl; and
$R^8$ is H; and
$R^9$ is CH or N; and
$R^{10}$ is COOH; and
$R^{11}$ is H; and
a is 0, 1, 2 or 3; and
b is 1, 2 or 3; and
c is 0 or 1; and
d is 0 or 1; and
e is 0 or 1; and
f is 1; and
g is 0; and
L is $CHR^{17}$ or O; and
$R^{17}$ is H or $C_{1-3}$ alkyl;
with the proviso that when $R^3$ is O and b is 1 then L is not O.

In another embodiment of the invention
$R^1$ is C—$R^{11}$; and
$R^2$ is aromatic heterocycle, aryl or cycloalkenyl; and
$R^3$ is O; and
$R^4$ is aryl; and
$R^5$ is H, or halogen; and
$R^6$ is H; and
$R^7$ is H or $C_{1-6}$ alkyl; and
$R^8$ is H; and
$R^9$ is CH or N; and
$R^{10}$ is COOH; and
$R^{11}$ is H; and
a is 0, 1, 2 or 3; and
b is 1, 2 or 3; and
c is 0 or 1; and
d is 0 or 1; and
e is 0 or 1; and
f is 1; and
g is 0; and
L is $CHR^{17}$; and
$R^{17}$ is H.

In another embodiment of the invention
$R^1$ is C—$R^{11}$; and
$R^2$ is aromatic heterocycle or cycloalkenyl; and
$R^3$ is O or S; and
$R^4$ is aryl; and
$R^5$ is H, —$OC_{1-3}$ alkyl or halogen; and
$R^6$ is H; and
$R^9$ is N; and
$R^{10}$ is COOH; and
$R^{11}$ is H; and
a is 0, 1, 2 or 3; and
b is 1, 2 or 3; and
c is 0; and
d is 0; and
e is 1; and
f is 1; and
g is 0; and
L is $CHR^{17}$ or O; and
$R^{17}$ is H or $C_{1-3}$ alkyl;
with the proviso that when $R^3$ is O or S and b is 1 then L is not O.

Compounds of the invention are:
1-{3-(3-furyl)-4-[(5-phenylpentyl)oxy]benzyl}azetidine-3-carboxylic acid;
1-{3-methoxy-4-[(5-phenylpentyl)oxy]-5-(2-thienyl)benzyl}azetidine-3-carboxylic acid;
1-{4-[(6-phenylhexyl)oxy]-3-(2-thienyl)benzyl}azetidine-3-carboxylic acid;
1-{4-[3-(benzyloxy)propoxy]-3-(2-thienyl)benzyl}azetidine-3-carboxylic acid;
1-{4-[3-(4-isobutylphenyl)propoxy]-3-(2-thienyl)benzyl}azetidine-3-carboxylic acid;
1-[4-(2-biphenyl-4-ylethoxy)-3-(2-thienyl)benzyl]azetidine-3-carboxylic acid;
1-{3-chloro-4-[(5-phenylpentyl)oxy]-5-(2-thienyl)benzyl}azetidine-3-carboxylic acid;
1-{3-chloro-4-[(5-phenylpentyl)oxy]-5-(2-thienyl)benzyl}azetidine-3-carboxylic acid;
1-{4-[(3-methyl-5-phenylpentyl)oxy]-3-(2-thienyl)benzyl}azetidine-3-carboxylic acid;
1-{3-(5-methyl-2-thienyl)-4-[(5-phenylpentyl)oxy]benzyl}azetidine-3-carboxylic acid;

1-{3-(4-methyl-2-thienyl)-4-[(5-phenylpentyl)oxy] benzyl}azetidine-3-carboxylic acid;
1-{3-(3-methyl-2-thienyl)-4-[(5-phenylpentyl)oxy] benzyl}azetidine-3-carboxylic acid;
1-{4-[(5-phenylpentyl)oxy]-3-(1,3-thiazol-5-yl) benzyl}azetidine-3-carboxylic acid;
1-{4-[(5-phenylpentyl)oxy]-3-(1,3-thiazol-4-yl) benzyl}azetidine-3-carboxylic acid;
1-{3-cyclopent-1-en-1-yl-4-[(5-phenylpentyl)oxy] benzyl}azetidine-3-carboxylic acid;
1-{4-[(5-phenylpentyl)oxy]-3-(2-thienyl)benzyl}azetidine-3-carboxylic acid;
1-{4-[(5-phenylpentyl)oxy]-3-(1H-pyrazol-5-yl) benzyl}azetidine-3-carboxylic acid;
1-{4-[(5-phenylpentyl)oxy]-3-(1H-pyrazol-4-yl) benzyl}azetidine-3-carboxylic acid;
1-{4-[(5-phenylpentyl)oxy]-3-pyridin-4-ylbenzyl}azetidine-3-carboxylic acid;
1-{4-[(5-phenylpentyl)oxy]-3-(3-thienyl)benzyl}azetidine-3-carboxylic acid;
1-({6-[(5-phenylpentyl)oxy]biphenyl-3-yl}methyl)azetidine-3-carboxylic acid;
1-{3-(2-furyl)-4-[(5-phenylpentyl)oxy]benzyl}azetidine-3-carboxylic acid;
1-{4-[(5-phenylpentyl)oxy]-3-(1,3-thiazol-2-yl) benzyl}azetidine-3-carboxylic acid;
1-{3-(1,3-oxazol-2-yl)-4-[(5-phenylpentyl)oxy] benzyl}azetidine-3-carboxylic acid;
1-{4-[(5-phenylpentyl)oxy]-3-(1H-pyrazol-1-yl) benzyl}azetidine-3-carboxylic acid;
1-{4-[(5-phenylpentyl)thio]-3-(2-thienyl)benzyl}azetidine-3-carboxylic acid;
1-{3-cyclopent-1-en-1-yl-4-[(5-phenylpentyl)thio] benzyl}azetidine-3-carboxylic acid;
3-({4-[(5-phenylpentyl)oxy]-3-(2-thienyl)benzyl}amino) cyclobutanecarboxylic acid;
3-[(1-{4-[(5-phenylpentyl)oxy]-3-(2-thienyl)phenyl}ethyl) amino]cyclobutanecarboxylic acid.
Preferred compounds of the invention are:
1-{3-(3-furyl)-4-[(5-phenylpentyl)oxy]benzyl}azetidine-3-carboxylic acid;
1-{3-chloro-4-[(5-phenylpentyl)oxy]-5-(2-thienyl) benzyl}azetidine-3-carboxylic acid;
1-{4-[(5-phenylpentyl)oxy]-3-(1,3-thiazol-5-yl) benzyl}azetidine-3-carboxylic acid;
1-{4-[(5-phenylpentyl)oxy]-3-(1,3-thiazol-4-yl) benzyl}azetidine-3-carboxylic acid;
1-{3-cyclopent-1-en-1-yl-4-[(5-phenylpentyl)oxy] benzyl}azetidine-3-carboxylic acid;
1-{4-[(5-phenylpentyl)oxy]-3-(2-thienyl)benzyl}azetidine-3-carboxylic acid;
1-{4-[(5-phenylpentyl)oxy]-3-(1H-pyrazol-5-yl) benzyl}azetidine-3-carboxylic acid;
1-{4-[(5-phenylpentyl)oxy]-3-(1H-pyrazol-4-yl) benzyl}azetidine-3-carboxylic acid;
1-{4-[(5-phenylpentyl)oxy]-3-(3-thienyl)benzyl}azetidine-3-carboxylic acid;
1-{3-(2-furyl)-4-[(5-phenylpentyl)oxy]benzyl}azetidine-3-carboxylic acid;
1-{4-[(5-phenylpentyl)oxy]-3-(1,3-thiazol-2-yl) benzyl}azetidine-3-carboxylic acid;
1-{3-(1,3-oxazol-2-yl)-4-[(5-phenylpentyl)oxy] benzyl}azetidine-3-carboxylic acid;
1-{4-[(5-phenylpentyl)oxy]-3-(1H-pyrazol-1-yl) benzyl}azetidine-3-carboxylic acid;
3-({4-[(5-phenylpentyl)oxy]-3-(2-thienyl)benzyl}amino) cyclobutanecarboxylic acid;
3-[(1-{4-[(5-phenylpentyl)oxy]-3-(2-thienyl)phenyl}ethyl) amino]cyclobutanecarboxylic acid.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, a hydrohalic acid, such as hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically. Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation: not limited to the treatment of diabetic retinopathy, other retinal degenerative conditions, dry eye, angiogenesis and wounds.

Therapeutic utilities related to the S1P receptors are ocular diseases, such as but not limited to: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases such as but not limited to: various inflammatory diseases, including acute lung injury, its prevention, sepsis, tumor metastasis, atherosclerosis, pulmonary edemas, and ventilation-induced lung injury; or autoimmune diseases and immunosuppression such as but not limited to: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation; or allergies and other inflammatory diseases such as but not limited to: urticaria, bronchial asthma, and other airway inflammations including pulmonary emphysema and chronic obstructive pulmonary diseases; or cardiac protection such as but not limited to: ischemia reperfusion injury and atherosclerosis; or wound healing such as but not limited to: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation such as but not limited to: treatment of osteoporosis and various bone fractures including hip and ankles; or anti-nociceptive activity such as but not limited to: visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular disease, wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases, various inflammatory diseases, including acute lung injury, its prevention, sepsis, tumor metastasis, atherosclerosis, pulmonary edemas, and ventilation-induced lung injury; or autoimmune diseases and immunosuppression, rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation; or allergies and other inflammatory diseases, urticaria, bronchial asthma, and other airway inflammations including pulmonary emphysema and chronic obstructive pulmonary diseases; or cardiac protection, ischemia reperfusion injury and atherosclerosis; or wound healing, scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation, treatment of osteoporosis and various bone fractures including hip and ankles; or anti-nociceptive activity, visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. The synthetic schemes set forth below, illustrate how compounds according to the invention can be made. Those skilled in the art will be able to routinely modify and/or adapt the following scheme to synthesize any compounds of the invention covered by Formula I.

In Scheme 1, hydroxybenzaldehydes react with hydroxylated compounds in the presence of triphenylphosphine and diethyl azodicarboxylate to give the corresponding ether intermediate. This intermediate is coupled with the boronic acid or the stannate of the corresponding $R^2$ group to give the corresponding intermediate. This intermediate reacts with azetidine-3-carboxylic acid in reductive amination conditions to give a derivative of Formula I.

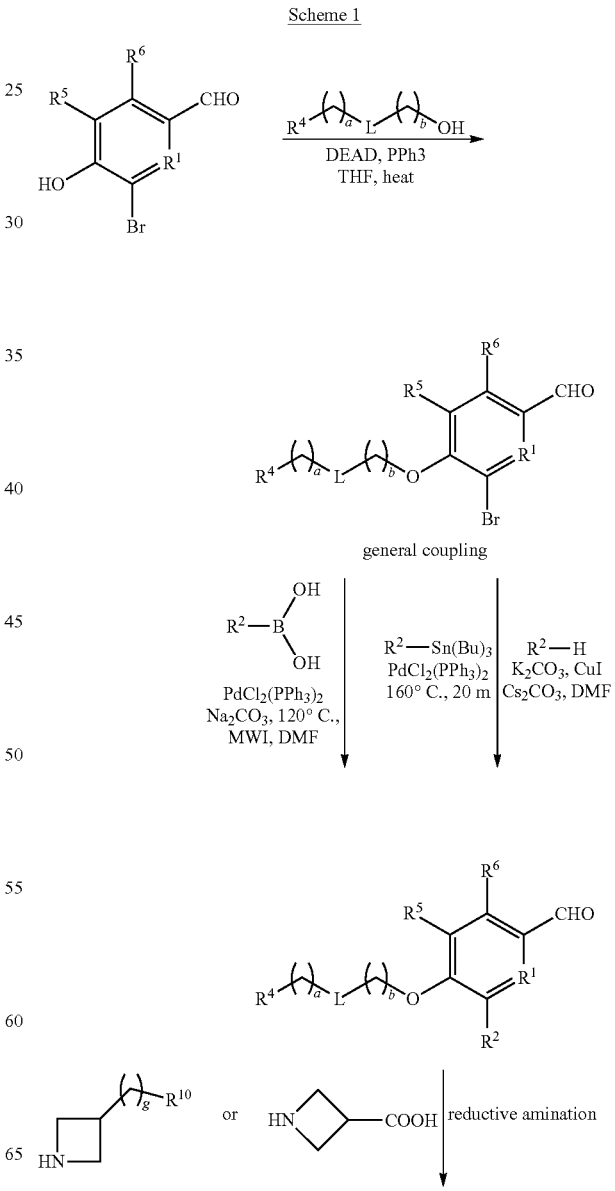

Scheme 1

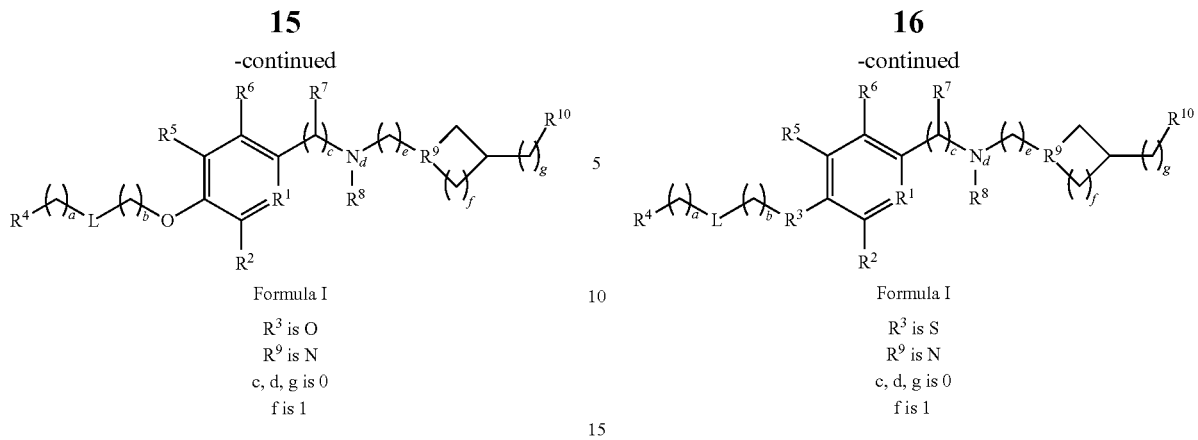

Formula I
R³ is O
R⁹ is N
c, d, g is 0
f is 1

Formula I
R³ is S
R⁹ is N
c, d, g is 0
f is 1

In Scheme 2, mercaptobenzaldehydes react with brominated compounds in the presence of triethylamine to give the corresponding thio intermediate. This intermediate is coupled with the boronic acid or the stannate of the corresponding R² group to give the corresponding intermediate. This intermediate reacts with azetidine-3-carboxylic acid in reductive amination conditions to give a derivative of Formula I.

In Scheme 3, ether or thio intermediates, obtained as described in Schemes 1 or 2 react with ethyl 3-aminocyclobutanecarboxylate-HCl salt in the presence of Sodium triacetoxyborohydride to give a derivative of Formula I.

Scheme 3

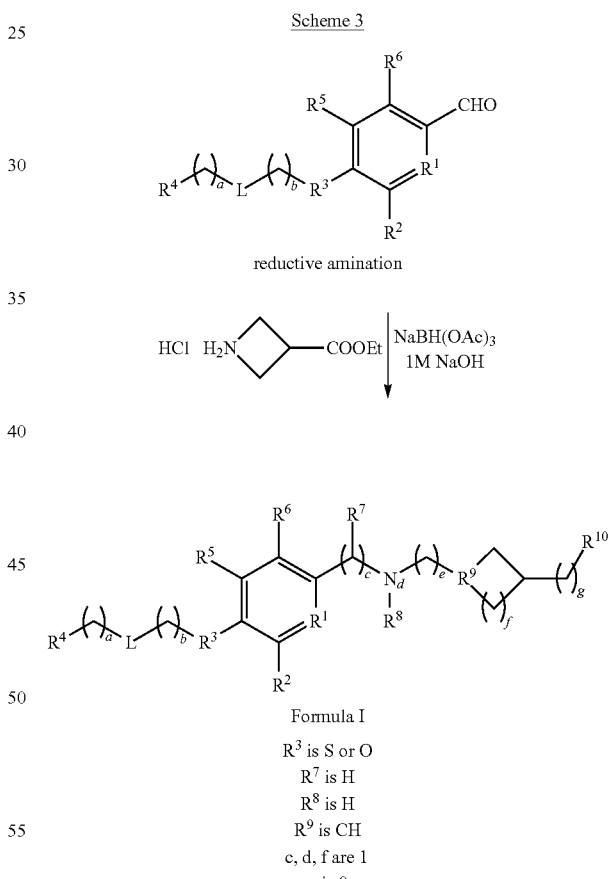

Formula I
R³ is S or O
R⁷ is H
R⁸ is H
R⁹ is CH
c, d, f are 1
g is 0

Scheme 2

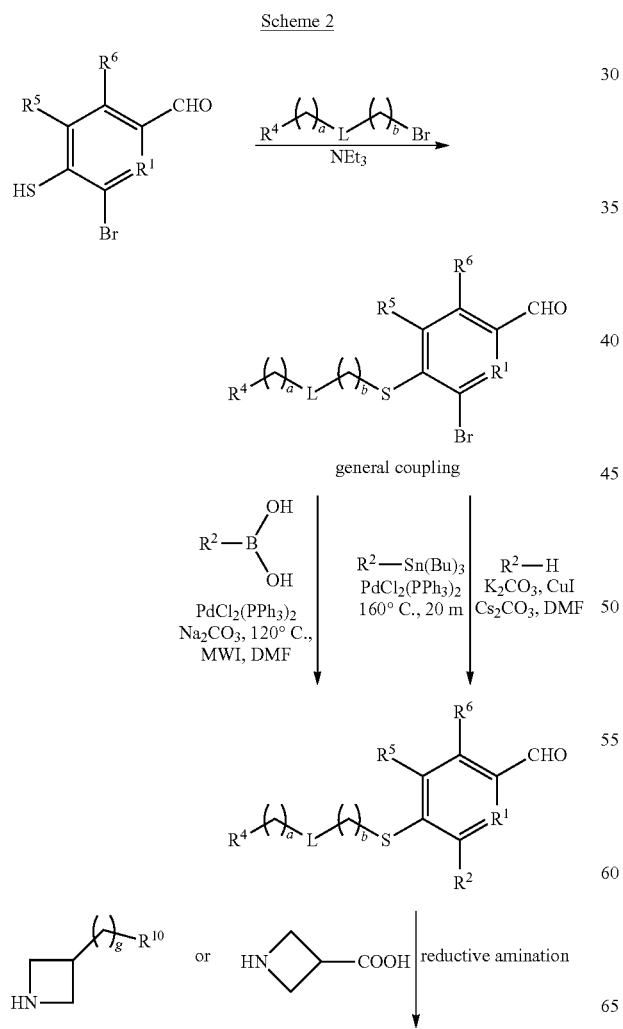

In Scheme 4, ether or thio intermediates, obtained as described in Schemes 1 or 2 react with an alkylmagnesium bromide derivative and ethyl 3-aminocyclobutanecarboxylate-HCl salt in the presence of magnesium oxide to give a derivative of Formula I.

Scheme 4

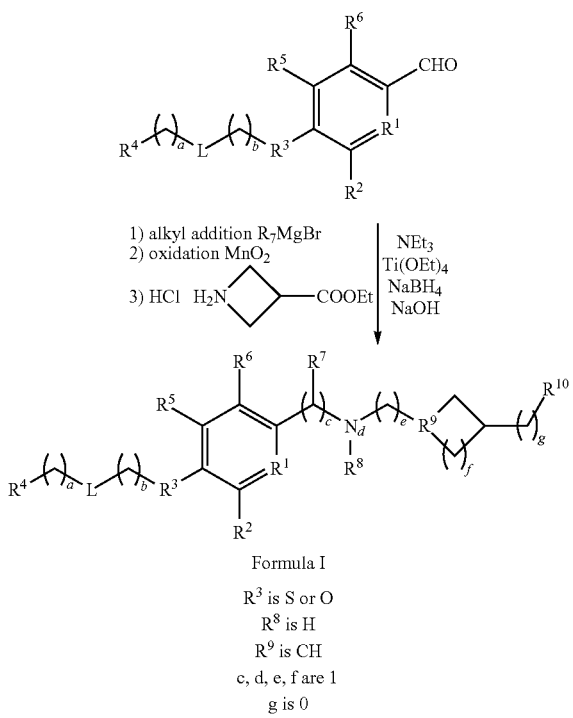

Formula I

R³ is S or O
R⁸ is H
R⁹ is CH
c, d, e, f are 1
g is 0

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of protium $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

Compound names were generated with ACD version 8; and Intermediates and reagent names used in the examples were generated with software such as Chem Bio Draw Ultra version 12.0 or Auto Nom 2000 from MDL ISIS Draw 2.5 SP1. In general, characterization of the compounds is performed according to the following methods:

NMR spectra are recorded on 300 and/or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by column chromatography (Auto-column) on a Teledyne-ISCO CombiFlash with a silica column, unless noted otherwise.

The following abbreviations are used in the examples:
s, m, h, d second, minute, hour, day
$NH_3$ ammonia
$CH_3CN$ acetonitrile
PSI pound per square inch
DCM dichloromethane
DMF N,N-dimethylformamide
NaOH sodium hydroxide
MeOH methanol
$CD_3OD$ deuterated methanol
$NH_3$ ammonia
HCl hydrochloric acid
$Na_2SO_4$ sodium sulfate
Si—CBH Silica bonded cyanoborohydride
rt room temperature
$MgSO_4$ magnesium sulfate
EtOAc ethyl acetate
$CDCl_3$ deuterated chloroform
DMSO-$d_6$ deuterated dimethyl sulfoxide
Auto-column automated flash liquid chromatography
TFA trifluoroacetic acid
THF tetrahydrofuran
$NaHB(OAc)_3$ sodium triacetoxyborohydride
DEAD diethyl azodicarboxylate
$Na_2CO_3$ sodium carbonate
$Cs_2CO_3$ cesium carbonate
M molar
$PdCl_2(PPh_3)_2$ bis(triphenylphosphine)palladium(II) chloride
AcOH acetic acid
$K_2CO_3$ potassium carbonate
CuI copper iodide
$MnO_2$ magnesium oxide
$MgCl_2$ magnesium chloride
NaCl sodium chloride
$Ti(OEt)_4$ titanium ethoxide
MeMgBr methylmagnesium bromide
$CHCl_3$ chloroform The following synthetic schemes illustrate how compounds according to the invention can be made. Those skilled in the art will be routinely able to modify and/or adapt the following schemes to synthesize any compound of the invention covered by Formula I.

Example 1

Compound 1

1-{3-(3-furyl)-4-[(5-phenylpentyl)oxy]benzyl}azetidine-3-carboxylic acid

Step-1:
A solution of 5-phenyl-pentan-1-ol [CAS 10521-91-2] (4.50 mL, 26.6 mmol), 3-bromo-4-hydroxybenzaldehyde [CAS 2973-78-6] (5.36 g, 26.7 mmol), triphenylphosphine (9.1 g, 34.6 mmol) and DEAD (14.5 mL, 40% in toluene, ~1.2 eqv) in THF (100 mL) was reacted at rt for 1 h, followed by heating to 60° C. for 2 days. Silica gel was added and the solvents were removed under vacuum. Chromatography on an Teledyne-ISCO CombiFlash with a silica column (auto-column) with 9.5 Hexanes/0.5 EtOAC to 9 Hexanes/1 EtOAc gave Intermediate 1: 3-bromo-4-(5-phenyl-pentyloxy)-benzldehyde as a clear oil that solidified upon standing, 5.38 g (58%).
$^1$H NMR (300 MHz, CDCl$_3$): δ 9.83 (s, 1H), 8.07 (d, J=2.1 Hz, 1H), 7.78 (dd, J=8.7, 2.1 Hz, 1H), 7.28-7.18 (m, 5H), 6.96 (d, J=8.4 Hz, 1H), 4.11 (t, J=6.3 Hz, 2H), 2.67 (t, J=7.2 Hz, 2H), 1.92-1.55 (m, 6H).

Step-2:
Intermediate 1 (290 mg, 0.87 mmol) in DMF (12 mL) was reacted with furan-3-yl boronic acid [CAS 5552-70-0] (195 mg, 1.74 mmol) Na$_2$CO$_3$ (2.8 mL, 2M) and PdCl$_2$(PPh$_3$)$_2$ (69 mg, ~11 mol %) at 120° C. for 20 m with MWI (microwave irradiation: Biotage Initiator 2.5). The reaction mixture was diluted with water, and extracted (two times) with 1:1 EtOAc: Hexanes (200 mL). The organic layers were washed with water (three times), dried over MgSO$_4$, filtered and concentrated onto silica gel. Auto-column (9 Hexanes/1 EtOAc) gave Intermediate 2: 3-(furan-3-yl)-4-((5-phenylpentyl)oxy)benzaldehyde 230 mg (29%).
$^1$H NMR (300 MHz, CDCl$_3$): δ 9.92 (s, 1H), 8.03 (d, J=2.4 Hz, 1H), 7.75-7.72 (m, 1H), 7.48 (s, 15H), 7.30-7.16 (m, 3H), 7.19-7.16 (m, 3H), 7.02 (d, J=8.7 Hz, 1H), 6.85 (d, J=1.2 Hz, 1H), 4.14 (t, J=6.3 Hz, 2H), 2.70-2.60 (m, 2H), 2.01-1.50 (series of m, 6H).

Step-3:
A solution of Intermediate 2 (230 mg, 0.66 mmol) and azetidine-3-carboxylic acid [CAS 36476-78-5] (66 mg, 0.65 mmol) in AcOH (0.2 mL), THF (2 mL) and MeOH (10 mL) was treated with Si—CBH, silica bonded cyanoborohydride (0.71 g, 0.93 mmol/g on silica gel support) and the mixture was reacted at rt for ~16-18 h. The mixture was concentrated onto silica gel and the solvent was removed under vacuum. Auto-column (25→40% MeOH: CH$_2$Cl$_2$) gave a white solid of the title compound: 1-{3-(3-furyl)-4-[(5-phenylpentyl)oxy]benzyl}azetidine-3-carboxylic acid 189 mg (69%).
$^1$H NMR (300 MHz, CD$_3$OD): δ 8.02 (s, 1H), 7.64 (d, J=2.4 Hz, 1H), 7.53 (t, J=1.8 Hz, 1H), 7.30-7.20 (m, 3H), 7.16-7.0 (m, 3H), 7.06 (d, J=8.7 Hz, 1H), 6.90 (d, J=1.2 Hz, 1H), 4.26 (s, 2H), 4.14-4.07 (m, 6H), 3.40-3.33 (m, 1H), 2.63 (t, J=7.8 Hz, 2H), 1.94-1.84 (m, 2H), 1.75-1.65 (m, 2H), 1.58-1.48 (m, 2H).

Compounds 2-21 were prepared from the corresponding benzaldehyde, and azetidine-3-carboxylic acid in a similar manner to the procedure described in Example 1 for Compound 1. The reagents used and the results are described below in Table 1.

TABLE 1

| Compound number | IUPAC name | Reagent(s) used | $^1$H NMR δ (ppm) for Compound |
|---|---|---|---|
| 2 | 1-{3-methoxy-4-[(5-phenylpentyl)oxy]-5-(2-thienyl)benzyl}azetidine-3-carboxylic acid | 5-phenyl-pentan-1-ol [CAS 10521-91-2] 3-bromo-4-hydroxy-5-methoxybenzaldehyde [CAS 2973-76-4] thiophen-2-yl boronic acid [CAS 13331-23-2] | (300 MHz, CD$_3$OD): δ 7.52 (dd, J = 0.9, 3.6 Hz, 1H), 7.43 (dd, J = 0.6, 4.8 Hz, 1H), 7.37 (d, J = 0.9 Hz, 1H), 7.26-7.21 (m, 2H), 7.15-7.13 (m, 3H), 7.08 (dd, J = 3.6, 4.8 Hz, 1H), 7.04 (d, J = 1.8 Hz, 1H), 4.28 (s, 2H), 4.17 (d, J = 8.4 Hz, 4H), 3.96-3.83 (m, 2H), 3.8 (s, 3H), 3.44-3.34 (m, 1H), 2.58 (t, J = 7.8 Hz, 1H), 1.81-1.72 (m, 2H), 1.67-1.57 (m, 2H), 1.49-1.39 (m, 2H) |
| 3 | 1-{4-[(6-phenylhexyl)oxy]-3-(2-thienyl)benzyl}azetidine-3-carboxylic acid | 3-bromo-4-hydroxybenzaldehyde [CAS 2973-78-6] 6-phenylhexan-1-ol [CAS 2430-16-2] thiophen-2-yl boronic acid [CAS 13331-23-2] | (300 MHz, CDCl$_3$): δ 7.72 (d, J = 1.8 Hz, 1H), 7.50 (d, J = 2.7 Hz, 1H), 7.28-7.24 (m, 4H), 7.18-7.15 (m, 3H), 7.01 (dd, J = 3.9, 5.1 Hz, 1H), 6.87 (d, J = 8.7 Hz, 1H), 4.05-3.96 (m, 8H), 3.40-3.35 (m, 1H), 2.60 (t, J = 7.8 Hz, 2H), 1.90-1.80 (m, 2H), 1.69-1.59 (m, 2H), 1.56-1.48 (m, 2H), 1.44-1.37 (m, 2H). |
| 4 | 1-{4-[3-(benzyloxy)propoxy]-3-(2-thienyl)benzyl}azetidine-3-carboxylic acid | 3-bromo-4-hydroxybenzaldehyde [CAS 2973-78-6] 3-(benzyloxy)propan-1-ol [CAS 4799-68-2] thiophen-2-yl boronic acid [CAS 13331-23-2] | (300 MHz, CDCl$_3$): δ 7.73 (s, 1H), 7.47 (d, J = 3.0 Hz, 1H), 7.30-7.24 (m, 7H), 7.01-6.98 (m, 1H), 6.91 (d, J = 8.4 Hz, 1H), 4.49 (s, 2H), 4.16 (t, J = 6.3 Hz, 2H), 4.08-3.97 (m, 6H), 3.70 (t, J = 6.0 Hz, 2H), 3.44-3.36 (m, 1H), 2.20-2.13 (m, 2H) |

TABLE 1-continued

| Compound number | IUPAC name | Reagent(s) used | $^1$H NMR δ (ppm) for Compound |
|---|---|---|---|
| 5 | 1-{4-[3-(4-isobutylphenyl)propoxy]-3-(2-thienyl)benzyl}azetidine-3-carboxylic acid | 3-bromo-4-hydroxybenzaldehyde [CAS 2973-78-6] 3-(4-isobutylphenyl)propan-1-ol [CAS 147598-21-8] thiophen-2-yl boronic acid [CAS 13331-23-2] | (300 MHz, CDCl$_3$): δ 7.74 (s, 1H), 7.52 (d, J = 2.7 Hz, 1H), 7.29-7.22 (m, 2H), 7.11-7.01 (m, 5H), 6.86 (d, J = 8.7 Hz, 1H), 4.06-4.01 (m, 8H), 3.42-3.36 (m, 1H), 2.82 (t, J = 7.8 Hz, 2H), 2.43 (d, J = 6.9 Hz, 2H), 2.22-2.14 (m, 2H), 1.90-1.76 (m, 1H), 0.89 (d, J = 6.6 Hz, 6H). |
| 6 | 1-[4-(2-biphenyl-4-ylethoxy)-3-(2-thienyl)benzyl]azetidine-3-carboxylic acid | 3-bromo-4-hydroxybenzaldehyde [CAS 2973-78-6] 2-(biphenyl-4-yl)ethanol [CAS 37729-18-3] thiophen-2-yl boronic acid [CAS 13331-23-2] | (300 MHz, CDCl$_3$-CD$_3$OD): δ 7.67 (d, J = 1.8 Hz, 1H), 7.59-7.53 (m, 4H), 7.47-7.41 (m, 3H), 7.38-7.32 (m, 4H), 7.27 (d, J = 8.7 Hz, 1H), 7.07-7.04 (m, 1H), 6.99 (d, J = 8.1 Hz, 1H), 4.34 (t, J = 6.9 Hz, 2H), 4.15-4.10 9m, 4H), 3.95 (t, J = 9.3 Hz, 2H), 3.30-3.24 (m, 3H). |
| 7 | 1-{3-chloro-4-[(5-phenylpentyl)oxy]-5-(2-thienyl)benzyl}azetidine-3-carboxylic acid | 3-bromo-5-chloro-4-hydroxy-benzaldehyde [CAS 2973-78-6] 5-phenyl-pentan-1-ol [CAS 10521-91-2] thiophen-2-yl boronic acid [CAS 13331-23-2] | (300 MHz, CDCl$_3$): δ 7.66 (d, J = 2.1 Hz, 1H), 7.54 (d, J = 2.7 Hz, 1H), 7.51 (d, J = 4.8 Hz, 1H), 7.45 (d, J = 1.8 Hz, 1H), 7.26-7.21 (m, 2H), 7.16-7.10 (m, 4H), 4.17 (s, 2H), 4.09-3.98 (m, 14H), 3.82 (t, J = 6.3 Hz, 2H), 3.42-3.34 (m, 1H), 2.61 (t, J = 7.8 Hz, 2H), 1.85-1.76 (m, 2H), 1.68-1.58 (m, 2H), 1.53-1.45 (m, 2H). |
| 8 | 1-{3-chloro-4-[(5-phenylpentyl)oxy]-5-(2-thienyl)benzyl}azetidine-3-carboxylic acid | 3-bromo-5-chloro-4-hydroxy-benzaldehyde, [CAS 2973-78-6] 2-(4-isobutylphenyl)ethanol [CAS 36039-35-7] thiophen-2-yl boronic acid [CAS 13331-23-2] | (300 MHz, CD$_3$OD): δ 7.74 (d, J = 1.8 Hz, 1H), 7.45 (d, J = 3.6 Hz, 1H), 7.38 (d, J = 8.7 Hz, 1H), 7.20 (d, J = 8.1 Hz, 2H), 7.13 (d, J = 8.7 Hz, 1H), 7.07-7.03 (m, 3H), 4.35 (t, J = 6.9 Hz, 2H), 4.27 (s, 2H), 4.13 (d, J = 8.4 Hz, 4H), 3.45-3.34 (m, 1H), 3.15 (t, J = 6.9 Hz, 2H), 2.43 (d, J = 7.2 Hz, 2H), 1.87-1.77 (m, 1H), 0.88 (d, J = 6.6 Hz, 6H). |
| 9 | 1-{4-[(3-methyl-5-phenylpentyl)oxy]-3-(2-thienyl)benzyl}azetidine-3-carboxylic acid | 3-bromo-5-chloro-4-hydroxy-benzaldehyde, [CAS 2973-78-6] 3-methyl-5-phenylpentan-1-ol [CAS 55066-48-3] thiophen-2-yl boronic acid [CAS 13331-23-2] | (300 MHz, CD$_3$OD): δ 7.77 (d, J = 2.1 Hz, 1H) 7.54 (dd, J = 0.9, 3.6 Hz, 1H), 7.38 (d, J = 5.1 Hz, 1H), 7.32 (dd, J = 2.1, 8.4 Hz, 1H), 7.23-7.18 (m, 2H), 7.14-7.04 (m, 5H), 4.26 (s, 2H), 4.17-4.11 (m, 6H), 3.42-3.33 (m, 1H), 2.72-2.52 (m, 2H), 2.04-1.91 (m, 1H), 1.85-1.63 (m, 3H), 1.56-1.44 (m, 1H), 1.00 (d, J = 6.6 Hz, 3H). |
| 10 | 1-{3-(5-methyl-2-thienyl)-4-[(5-phenylpentyl)oxy]benzyl}azetidine-3-carboxylic acid | Intermediate 1 (5-methylthiophen-2-yl)boronic acid [CAS 162607-20-7] | (300 MHz, CD$_3$OD): δ 7.70 (d, J = 2.1 Hz, 1H), 7.34 (d, J = 3.3 Hz, 1H), 7.29-7.20 9m, 3H), 7.16-7.12 (m, 2H), 7.07 (d, J = 8.4 Hz, 1H), 6.73 (d, J = 2.4 Hz, 1H), 4.25 (S, 2H), 4.14-4.08 (m, 6H), 3.42-3.33 (m, 1H), 2.63 (t, J = 7.5 Hz, 2H), 2.47 (s, 3H), 1.94-1.86 (m, 2H), 1.76-1.66 (m, 2H), 1.62-1.52 (m, 2H) |
| 11 | 1-{3-(4-methyl-2-thienyl)-4-[(5-phenylpentyl)oxy]benzyl}azetidine-3-carboxylic acid | Intermediate 1 (4-methylthiophen-2-yl)boronic acid [CAS 162607-15-0] | (300 MHz, CD$_3$OD): δ 7.74 (d, J = 2.1 Hz, 1H), 7.39 (s, 1H), 7.29 (dd, J = 2.1, 8.4 Hz, 1H), 7.25-7.20 (m, 2H), 7.16-7.12 (m, 3H), 7.08 (d, J = 8.7 Hz, 1H), 6.97 (s, 1H), 4.26 (s, 2H), 4.14-4.08 (m, 6H), 3.37 (t, J = 7.8 Hz, 2H), 2.26 (s, 3H), 1.94-1.85 (m, 2H), 1.72-1.65 (m, 2H), 1.62-1.57 9m, 2H). |

TABLE 1-continued

| Compound number | IUPAC name | Reagent(s) used | $^1$H NMR δ (ppm) for Compound |
|---|---|---|---|
| 12 | 1-{3-(3-methyl-2-thienyl)-4-[(5-phenylpentyl)oxy]benzyl}azetidine-3-carboxylic acid | Intermediate 1 (3-methylthiophen-2-yl)boronic acid [CAS 177735-09-0] | (300 MHz, CD$_3$OD): δ 7.41 (dd, J = 1.8, 8.1 Hz, 1H), 7.35 (d, J = 2.1 Hz, 1H), 7.28 (d, J = 5.1 Hz, 1H), 7.24-7.20 (m, 2H), 7.14-7.08 (m, 4H), 6.88 (d, J = 5.1 Hz, 1H), 4.28 (s, 2H), 4.14 (d, J = 8.1 Hz, 4H) 3.98 (t, J = 6.0 Hz, 2H), 3.42-3.36 (m, 1H), 2.54 (t, J = 7.8 Hz, 2H), 2.08 (s, 3H), 1.76-1.67 (m, 2H), 1.63-1.53 (m, 2H), 1.44-1.36 (m, 2H). |
| 13 | 1-{4-[(5-phenylpentyl)oxy]-3-(1,3-thiazol-5-yl)benzyl}azetidine-3-carboxylic acid | Intermediate 1 5-(4,4,5,5-tetramethyl-1,3,2-dioxaborolan-2-yl)thiazole [CAS 1086111-09-2] | (300 MHz, CD$_3$OD): δ 8.93 (s, 1H), 8.33 (s, 1H), 7.80 (d, J = 1.8 Hz, 1H), 7.37 (dd, J = 2.1, 8.4 Hz, 1H), 7.25-7.20 (m, 2H), 7.16-7.11 (m, 4H), 4.14 (t, J = 6.3 Hz, 2H), 4.06 (s, 2H), 3.98-3.84 9m, 4H), 3.38-3.30 (m, 1H), 2.63 (t, J = 7.5 Hz, 2H), 1.95-1.86 (m, 3H), 1.76-1.86 9m, 2H), 1.76-1.66 (m, 2H), 1.61-1.53 (m, 2H). |
| 14 | 1-{4-[(5-phenylpentyl)oxy]-3-(1,3-thiazol-4-yl)benzyl}azetidine-3-carboxylic acid | Intermediate 1 4-(4,4,5,5-tetramethyl-1,3,2-dioxaborolan-2-yl)thiazole [CAS 1083180-00-0] | (300 MHz, CD$_3$OD): δ 8.98 (d, J = 1.5 Hz, 1H), 8.23 (d, J = 1.8 Hz, 1H), 7.99 (d, J = 1.8, 1H), 7.39 (dd, J = 2.1, 8.4 Hz, 1H), 7.26-7.20 (m, 2H), 7.15-7.09 (m, 4H), 4.27 (s, 2H), 4.16-4.10 (m, 6H), 3.42-3.33 (m, 1H), 2.62 (t, J = 7.5 Hz, 2H), 1.95-1.85 (m, 2H), 1.74-1.65 (m, 2H), 1.56-1.46 (m, 2H). |
| 15 | 1-{3-cyclopent-1-en-1-yl-4-[(5-phenylpentyl)oxy]benzyl}azetidine-3-carboxylic acid | Intermediate 1 cyclopent-1-en-1-ylboronic acid [CAS 850036-28-1] | (300 MHz, CD$_3$OD): δ 7.33 (d, J = 2.1 Hz, 1H), 7.26-7.20 (m, 3H), 7.16-7.10 (m, 3H), 6.98 (d, J = 8.7 Hz, 1H), 6.40 (brs, 1H), 4.23 (s, 2H), 4.12 (d, J = 8.4 Hz, 4H), 4.01 (t, J = 6.3 Hz, 2H), 3.42-3.33 (m, 1H), 2.75-2.69 (m, 2H), 2.62 (t, J = 7.8 Hz, 2H), 2.51-2.45 (m, 2H), 1.97-1.79 (m, 4H), 1.74-1.64 (m, 2H), 1.56-1.46 (m, 2H). |
| 16 | 1-{4-[(5-phenylpentyl)oxy]-3-(2-thienyl)benzyl}azetidine-3-carboxylic acid | Intermediate 1 thiophen-2-ylboronic acid [CAS 13331-23-2] | (300 MHz, CD$_3$OD): δ 7.77 (d, J = 2.1 Hz, 1H), 7.54 (d, J = 3.3 Hz, 1H), 7.38 (d, J = 4.5 Hz, 1H), 7.30 (dd, J = 2.1, 8.7 Hz, 1H), 7.24-7.19 (m, 2H), 7.15-7.12 9m, 3H), 7.08-7.04 (m, 2H), 4.24 (s, 3H), 4.13-4.06 (m, 6H), 3.43-3.33 (m, 1H), 2.60 (t, J = 7.2 Hz, 2H), 1.94-1.82 (m, 2H), 1.73-1.63 (m, 2H), 1.62-1.51 (m, 2H). |
| 17 | 1-{4-[(5-phenylpentyl)oxy]-3-(1H-pyrazol-5-yl)benzyl}azetidine-3-carboxylic acid | Intermediate 1 (1H-pyrazol-5-yl)boronic acid [CAS 1239363-47-3] | (300 MHz, CD$_3$OD): δ 7.79 (d, J = 2.1 Hz, 1H), 7.60 (d, J = 2.1 Hz, 1H), 7.37 (dd, J = 2.1, 8.7 Hz, 1H), 7.24-7.20 (m, 2H), 7.15-7.09 (m, 4H), 6.73 (d, J = 2.1 Hz, 1H), 4.23 (s, 2H), 4.12-4.07 9m, 6H), 3.43-3.33 (m, 1H), 2.60 (t, J = 7.5 Hz, 2H), 1.92-1.82 (m, 2H), 1.73-1.62 (m, 2H), 1.55-1.44 (m, 2H). |
| 18 | 1-{4-[(5-phenylpentyl)oxy]-3-(1H-pyrazol-4-yl)benzyl}azetidine-3-carboxylic acid | Intermediate 1 (1H-pyrazol-4-yl)boronic acid [CAS 763120-58-7] | (300 MHz, CD$_3$OD): δ 8.07 (s, 2H), 7.69 (d, J = 2.4 Hz, 1H), 7.24-7.04 (m, 7H), 4.23 (s, 2H), 4.12-4.06 (m, 6H), 3.42-3.30 (m, 1H), 2.62 (t, J = 7.2, 2H), 1.95-1.85 (m, 2H), 1.75-1.64 (m, 2H), 1.60-1.50 9m, 2H). |

TABLE 1-continued

| Compound number | IUPAC name | Reagent(s) used | $^1$H NMR δ (ppm) for Compound |
|---|---|---|---|
| 19 | 1-{4-[(5-phenylpentyl)oxy]-3-pyridin-4-ylbenzyl}azetidine-3-carboxylic acid | Intermediate 1 pyridin-4-ylboronic acid [CAS 1692-15-5] | (300 MHz, CD$_3$OD): δ 8.48 (dd, J = 1.5, 4.5 Hz, 2H), 7.55 (dd, J = 1.8, 4.5 Hz, 2H), 7.50-7.48 (m, 2H), 7.26-7.19 (m, 2H), 7.15-7.10 (m, 4H), 4.26 (s, 2H), 4.13-4.10 (m, 4H), 4.03 (t, J = 6.3 Hz, 2H), 3.49-3.33 (m, 2H), 2.56 (t, J = 7.2 Hz, 2H), 1.79-1.69 (m, 2H), 1.66-1.56 (m, 2H), 1.45-1.35 (m, 2H). |
| 20 | 1-{4-[(5-phenylpentyl)oxy]-3-(3-thienyl)benzyl}azetidine-3-carboxylic acid | Intermediate 1 thiophen-3-ylboronic acid [CAS 5552-70-0] | (300 MHz, CD$_3$OD): δ 7.66 (dd, J = 1.2, 3.0 Hz, 1H), 7.60 (d, J = 1.2 Hz, 1H), 7.44 (dd, J = 1.2, 5.1 Hz, 1H), 7.38 (dd, J = 3.0, 4.8 Hz, 1H), 7.32 (dd, J = 2.1, 8.4 Hz, 1H), 7.25-7.20 (m, 2H), 7.14 (d, J = 6.9 Hz, 3H), 7.08 (d, J = 8.7 Hz, 1H), 4.23 (s, 2H), 4.13 (d, J = 8.4 Hz, 4H), 4.05 (t, J = 6.6 Hz, 2H), 3.42-3.33 (m, 1H), 2.60 (t, J = 7.5 Hz, 2H), 2.60 (t, J = 7.5 Hz, 2H), 1.87-1.78 (m, 2H), 1.71-1.61 (m, 2H), 1.53-1.43 (m, 2H). |
| 21 | 1-({6-[(5-phenylpentyl)oxy]biphenyl-3-yl}methyl)azetidine-3-carboxylic acid | Intermediate 1 phenylboronic acid [CAS 98-80-6] | (300 MHz, CD$_3$OD): δ 7.46 (dd, J = 1.8, 8.1 Hz, 2H), 7.34-7.28 (m, 5H), 7.25-7.19 (m, 2H), 7.14-7.06 (m, 4H), 4.28 (s, 2H), 4.14 (d, J = 8.1 Hz, 4H), 3.98 (t, J = 6.0 Hz, 2H), 3.36 (pentet, J = 7.8 Hz, 1H), 2.54 (t, J = 7.8 Hz, 2H), 1.76-1.68 (m, 2H), 1.61-1.53 (m, 2H), 1.43-1.36 (m, 2H). |

Example 2

Compound 22

1-{3-(2-furyl)-4-[(5-phenylpentyl)oxy]benzyl}azetidine-3-carboxylic acid

Step-1:

Intermediate 1 (0.65 g, 1.87 mmol) in DMF (14 mL) was reacted with tributyl(furan-2-yl)stannane [CAS 118486-94-5] (1.2 mL, 3.70 mmol) and PdCl$_2$(PPh$_3$)$_2$ (0.197 g, ~15 mol %) at 160° C. for 15 m with MWI (microwave irradiation: Biotage Initiator 2.5). The reaction mixture was diluted with 2:1 EtOAc/Hexanes (~150 mL), washed with water (three times), and dried over MgSO$_4$, filtered and concentrated onto silica gel. Auto-column (9.5 Hexanes/0.5 EtOAc) gave Intermediate 3: 3-furan-2-yl-4-(5-phenyl-pentyloxy)-benzaldehyde as a white solid, 0.44 g (70%).

$^1$H NMR (300 MHz, CD$_3$OD): δ 9.94 (s, 1H), 8.37 (d, J=2.1 Hz, 1H), 7.77-7.74 (m, 1H), 7.49 (d, J=1.2 Hz, 1H), 7.30-7.10 (m, 5H), 7.04-6.90 (m, 2H), 6.50 (brs, 1H), 4.21-4.05 (m, 2H), 2.70-2.60 (m, 2H), 2.10-1.50 (series m, 6H).

Step 2:

Intermediate 3 reacted with azetidine-3-carboxylic acid as described in the procedure for Example 1 to produce the title compound: 1-{3-(2-furyl)-4-[(5-phenylpentyl)oxy]benzyl}azetidine-3-carboxylic acid.

$^1$H NMR (300 MHz, CD$_3$OD): δ 7.90 (s, 1H), 7.53 (s, 1H), 7.28 (t, J=8.1 Hz, 1H), 7.21 (d, J=6.9 Hz, 2H), 7.16-7.12 (m, 3H), 7.06 (d, J=8.7 Hz, 1H), 6.92 (d, J=3.3 Hz, 1H), 6.48 (s, 1H), 4.28 (s, 2H), 4.15-4.07 (s, 2H), 3.40-3.33 (m, 1H), 2.62 (t, J=7.2 Hz, 2H), 1.93-1.84 (m, 2H), 1.75-1.65 (m, 2H), 1.58-1.48 (m, 2H).

Compounds 23 and 24 were prepared from the corresponding stannate, and azetidine-3-carboxylic acid in a similar manner to the procedure described in Example 2 for Compound 22. The reagents used and the results are described below in Table 2.

TABLE 2

| | | | |
|---|---|---|---|
| 23 | 1-{4-[(5-phenylpentyl)oxy]-3-(1,3-thiazol-2-yl)benzyl}azetidine-3-carboxylic acid | Intermediate 1 2-(tributylstannyl)thiazole [CAS 121359-48-6] | (300 MHz, CD$_3$OD): δ 8.36 (d, J = 2.1 Hz, 1H), 7.88 (d, J = 3.3 Hz, 1H), 7.58 (d, J = 3.3 Hz, 1H), 7.49 (dd, J = 1.8, 8.4 Hz, 1H), 7.25-7.10 (m, 6H), 4.32 (s, 2H), 4.23 (t, J = 8.4 Hz, 4H), 3.34-3.42 (m, 1H), 2.64 (t, J = 7.2 Hz, 2H), 2.02-1.93 (m, 2H), 1.76-1.68 (m, 2H), 1.65-1.58 (m, 2H). |

TABLE 2-continued

| 24 | 1-{3-(1,3-oxazol-2-yl)-4-[(5-phenylpentyl)oxy]benzyl}azetidine-3-carboxylic acid | Intermediate 1 2-(tributylstannyl)oxazale [CAS 145214-05-7] | (300 MHz, CD$_3$OD): δ 7.91-7.90 (m, 2H), 7.56 (dd, J = 2.1, 8.4 Hz, 1H), 7.28 (s, 1H), 7.24-7.10 (m, 6H), 4.29 (s, 2H), 4.19-4.09 (m, 6H), 3.42-3.33 (m, 1H), 2.60 (t, J = 7.5 Hz, 2H), 1.88-1.79 (m, 2H), 1.71-1.62 (m, 2H), 1.55-1.45 (m, 2H). |
|---|---|---|---|

Example 3

Compound 25

1-{4-[(5-phenylpentyl)oxy]-3-(1H-pyrazol-1-yl)benzyl}azetidine-3-carboxylic acid Step 1:

A solution of Intermediate 1 (0.41 g, 1.18 mmol), K$_2$CO$_3$ (0.49 g, 3.54 mmol), CuI (0.23 g, 2.39 mmol), pyrazole [CAS 288-13-1] (0.18 g, 2.64 mmol) and N,N-dimethylethane-1,2-diamine (0.1 mL, 0.93 mmol) in dioxane was heated to 105° C. for 16-18 h. To the mixture was added Cs$_2$CO$_3$ (1.0 g, 3.07 mmol) Cu—Sn alloy (500 mg, 200 mesh) and DMF (~15 mL) and heating at 160° C. was continued for 16-18 h. The mixture was cooled to rt and subjected to a standard aqueous work-up. The crude material was purified on auto-column (8:2 Hexanes/EtOAc) to give Intermediate 4 as a white solid, 4-(5-phenylpentyloxy)-3-(1H-pyrazol-1-yl)benzaldehyde 120 mg (51%).

$^1$H NMR (300 MHz, CD$_3$OD): δ 9.94 (s, 1H), 8.31 (d, J=1.8 Hz, 1H), 8.05 (d, J=1.8 Hz, 1H), 7.84-7.80 (m, 1H), 7.79 (s, 1H), 7.29-7.24 (m, 2H), 7.78-7.11 (m, 4H), 6.42 (s, 1H), 4.14 (t, J=6.3 Hz, 2H), 2.63 (t, J=7.8 Hz, 2H), 1.83-1.39 (series of m, 6H).

Step 2:

Intermediate 4 reacted with azetidine-3-carboxylic acid as described in the procedure for Example 1 to produce the title compound: 1-{4-[(5-phenylpentyl)oxy]-3-(1H-pyrazol-1-yl)benzyl}azetidine-3-carboxylic acid.

$^1$H NMR (300 MHz, CD$_3$OD): δ 8.01 (d, J=2.1 Hz, 1H), 7.68 (dd, J=2.1, 7.8 Hz, 2H), 7.43 (dd, J=2.1, 8.4 Hz, 1H), 7.25-7.20 (m, 3H), 6.44 (t, J=2.4 Hz, 1H), 4.26 (s, 2H), 4.16-4.04 (m, 6H), 3.40-3.32 (m, 1H), 2.58 (t, J=7.5 Hz, 2H), 1.83-1.74 (m, 2H), 1.68-1.58 (m, 2H), 1.47-1.39 (m, 2H).

Example 4

Compound 26

1-{4-[(5-phenylpentyl)thio]-3-(2-thienyl)benzyl}azetidine-3-carboxylic acid

Step-1:

A mixture of 3-bromo-4-fluorobenzaldehyde [CAS 77771-02-9] (5.1 g, 24.6 mmol) in DMF (25 mL) was treated with sodium sulfide Na$_2$S 9H$_2$O (6.80 g, 27.7 mmol) and the mixture was stirred at rt for 9 d. After an acidic workup and extraction with Hexanes/EtOAc (1:1) the pooled organic layers were washed with water (three times) and dried over MgSO$_4$, filtered and concentrated onto silica gel. Auto-column (9:1 hexane/EtOAc) gave Intermediate 5 as a solid 3.07 g (58%) 3-bromo-4-mercaptobenzaldehyde.

$^1$H NMR (300 MHz, CD$_3$OD): δ 9.86 (s, 1H), 7.98 (d, J=1.5 Hz, 1H), 7.64 (d, J=1.8 Hz, 1H), 7.47 (d, J=7.8 Hz, 1H), 4.31 (s, 1H).

Step-2:

A solution of Intermediate 5 (2.80 g, 11.3 mmol) and (5-bromopentyl)benzene [CAS 14469-83-1] (2.61 g, 11.5 mol) with triethylamine (3.1 mL) in THF (30 mL) was stirred at rt for 18 hr. The solvent was removed under vacuum and the residue was dissolved in EtOAc/Hexanes (200 mL, 1:1), washed with water, dried over MgSO$_4$, filtered and concentrated onto silica gel. Auto-column (9.5 Hexanes/0.5 EtOAc) gave Intermediate 6 an oil, 1.74 g (42%) 3-bromo-4-((5-phenylpentyl)thio)benzaldehyde.

$^1$H NMR (300 MHz, CDCl$_3$): δ 9.86 (s, 1H), 7.98 (d, J=1.8 Hz, 1H), 7.72 (dd, J=8.4, 1.2 Hz, 1H), 7.28-7.15 (m, 6H), 2.97 (t, J=7.5 Hz, 2H), 2.63 (t, J=7.5 Hz, 2H), 1.79-1.54 (series of m, 4H).

Step-3:

Intermediate 6 and thiophen-2-ylboronic acid reacted with azetidine-3-carboxylic acid as described in the procedure for Example 1 to produce the title compound: 1-{4-[(5-phenylpentyl)thio]-3-(2-thienyl)benzyl}azetidine-3-carboxylic acid.

$^1$H NMR (600 MHz, CD$_3$OD): δ 7.48-7.47 (m, 1H), 7.46-7.45 (m, 2H), 7.36 (dd, J=2.4, 8.4 Hz, 1H), 7.26-7.25 (m, 1H), 7.23-7.21 (m, 2H), 7.13-7.11 (m, 3H), 7.10 (dd, J=4.2, 5.4 Hz, 1H), 4.26 (s, 2H), 4.14-4.08 (m, 4H), 3.39-3.34 (m, 1H), 2.86 9t, J=7.8 Hz, 2H), 2.56 (t, J=7.8 Hz, 2H), 1.64-1.56 (m, 4H), 1.44-1.39 (m, 2H).

Example 5

Compound 27

1-{3-cyclopent-1-en-1-yl-4-[(5-phenylpentyl)thio]benzyl}azetidine-3-carboxylic acid The title compound was synthesized according to the procedure described in Example 4; wherein Intermediate 6 reacted with cyclopent-1-en-1-ylboronic acid in Step 3.

$^1$H NMR (600 MHz, CD$_3$OD): δ 7.34 (d, J=8.4, 1H), 7.26-7.21 (m, 4H), 7.14-7.11 (m, 3H), 5.91 (pentet, J=2.4 Hz, 1H), 4.23 (s, 2H), 4.13-4.08 (m, 4H), 3.39-3.33 (m, 1H), 2.90 (t, J=7.8 Hz, 2H), 2.73-2.70 (m, 2H), 2.58 (t, J=7.2 Hz, 2H), 2.54-2.50 9 m, 2H), 2.03-1.98 (m, 2H), 1.66-1.59 (m, 4H), 1.48-1.43 (m, 2H).

Example 6

Compound 28

3-({4-[(5-phenylpentyl)oxy]-3-(2-thienyl)benzyl}amino)cyclobutanecarboxylic acid Step-1:

A solution of Intermediate 7: 4-((5-phenylpentyl)oxy)-3-(thiophen-2-yl)benzaldehyde [as produced during the synthesis of Compound 16, from Intermediate 1 and thiophen- 2-yl boronic acid] (230 mg, 0.66 mmol) and ethyl 3-aminocyclobutanecarboxylate-HCl salt [CAS 957793-35-0] (150 mg, 0.84 mmol) in THF (11 mL), acetic acid (1.2 mL) and EtOH (6 mL) was stirred at rt for 1 h. Intermediate 7: $^1$H NMR (300 MHz, CDCl$_3$): δ 9.92 (s, 1H), 8.17 (d, J=2.1 Hz, 1H), 7.75 (dd, J=9.9, 2.1 Hz, 1H), 7.56 (dd, J=3.6, 1.2 Hz, 1H), 7.37-7.02 (series of m, 8H), 4.16 (t, J=6.6 Hz, 2H), 2.66 (t, J=7.2 Hz, 2H), 2.01-1.54 (series of m, 6H). NaBH(OAc)$_3$ (320 mg, 1.43 mmol) was added and the mixture was stirred at rt for 18 h. Solvents were removed under vacuum and the mixture was treated with NaOH (1 M) to adjust pH>7. The mixture was extracted with EtOAc, and the organic layers were combined, dried over MgSO$_4$, filtered and concentrated onto silica gel. Auto column (EtOAc) gave Intermediate 8 as a clear oil, ethyl 3-((4-((5-phenylpentyl)oxy)-3-(thiophen-2-yl)benzyl)amino)cyclobutanecarboxylate.

$^1$H NMR (300 MHz, CDCl$_3$): δ 7.57 (d, J=1.8 Hz, 1H), 7.50 (dd, J=0.9, 2.7 Hz, 1H), 7.31-7.14 (m, 7H), 7.06 (dd, J=3.9, 1.5 Hz, 1H), 6.90 (d, J=8.4 Hz, 1H), 4.15-4.03 (m, 4H), 3.69 (s, 2H), 3.29-3.18 (m, 1H), 2.78-2.46 (m, 5H), 2.01-1.49 (series of m, 8H), 1.24 (t, J=6.9 Hz, 3H).

Step-2:

Intermediate 8 (200 mg, 0.42 mmol) in dioxane (10 mL) was treated with NaOH (3.5 mL, 1M) at rt for 1 h. Solvent was removed under vacuum and the pH was adjusted to 3-4 with HCl (1M). The solution was extracted with CHCl$_3$: isopropanol (3:1). The organic solvent was removed under vacuum to give the title compound: 3-({4-[(5-phenylpentyl)oxy]-3-(2-thienyl)benzyl}amino)cyclobutanecarboxylic acid.

$^1$H NMR (300 MHz, CD$_3$OD): δ 7.83 (d, J=2.1 Hz, 1H), 7.58 (dd, J=0.9, 3.9 Hz, 1H), 7.41 (d, J=5.4 Hz, 1H), 7.35 (dd, J=2.1, 8.4 Hz, 1H), 7.25-7.20 (m, 2H), 7.16-7.13 (m, 3H), 7.10-7.06 (m, 2H), 4.15-4.09 (m, 4H), 3.77 (pentet, J=8.4 Hz, 1H), 3.02 (pentet, J=9.0 Hz, 1H), 2.65-2.56 (m, 4H), 2.45-2.35 (m, 2H), 1.95-1.86 (m, 2H), 1.75-1.65 (m, 2H), 1.62-1.52 (m, 2H).

Example 7

Compound 29

3-[(1-{4-[(5-phenylpentyl)oxy]-3-thienyl)phenyl}ethyl)amino]cyclobutanecarboxylic acid Step-1:

A mixture of Intermediate 7 (600 mg, 1.71 mmol) in THF (15 mL) at −78° C. was reacted with MeMgBr (2.0 mL, 3.0 M in diethyl ether) and warmed to 0° C. for 3 h. The mixture was quenched with water, and THF removed under vacuum. The aqueous layer was extracted with EtOAc. The pooled organic extracts were dried ove MgSO$_4$, filtered, and concentrated onto silica gel. Auto-column (8.5 hexane/1.5 EtOAc) gave Intermediate 9, as an oil, 450 mg (72%): 1-(4-((5-phenylpentyl)oxy)-3-(thiophen-2-yl)phenyl)ethanol.

$^1$H NMR (600 MHz, CDCl$_3$): δ 7.63 (d, J=4.2 Hz, 1H), 7.49 (dd, J=1.2, 4.2 Hz, 1H), 7.29-7.16 (series of m, 7H), 7.05 (dd, J=3.6, 4.8 Hz, 1H), 6.87 (d, J=9.0 Hz, 1H), 4.83 (q, J=6.0 Hz, 1H), 4.02 (d, J=6.0 Hz, 2H), 2.63 (t, J=7.8 Hz, 2H), 1.91-1.54 (series of m, 6H), 1.48 (d, J=6.6 Hz, 3H).

Step-2:

A mixture of Intermediate 9 (450 mg, 1.23 mmol) and MnO$_2$ (1.1 g, 10.7 mmol (85%)) in dioxane (20 mL) was heated at 100° C. for 18 h. The mixture was filtered and solvent removed under vacuum. The residue was dissolved in chloroform and concentrated onto silica gel under reduced pressure. Auto-column (9 hexane: 1 EtOAc) gave Intermediate 10, as a white solid 350 mg (78%) 1-(4-((5-phenylpentyl)oxy)-3-(thiophen-2-yl)phenyl)ethanone. MS [M+23]$^+$ 387.19

Step-3:

3-Aminocyclobutanecarboxylate-HCl salt (260 mg, 1.45 mmol) in THF (8 mL) was treated with triethylamine (0.185 mL, 1.33 mmol) for 1 h at rt. Ti(OEt)$_4$ (0.32 mL) was added followed by Intermediate 10 (350 mg, 0.96 mmol) in THF (6 mL) at rt for 2.5 h. Sodium borohydride (190 mg) was added and the mixture was stirred at rt for ~18 h. Aqueous ammonium hydroxide (2.5 mL) was added and the mixture stirred for 1 h at rt. The solvent was removed and the mixture was diluted with EtOAc, water, and filtered through celite. The organic layer was separated and the aqueous layer was extracted with EtOAc. The organic was combined, dried over MgSO$_4$, filtered and concentrated onto silica gel. Auto-column (8 EtOAc: 2 Hexanes) gave Intermediate 11 as a clear oil 100 mg, (21%) ethyl 3-((1-(4-((5-phenylpentyl)oxy)-3-(thiophen-2-yl)phenyl)ethyl)amino)cyclobutanecarboxylate.

$^1$H NMR (600 MHz, CDCl$_3$): δ 7.56 (d, J=2.4 Hz, 1H), 7.51-7.50 (m, 1H), 7.31-7.25 (m, 3H), 7.19-7.15 (m, 4H), 7.06 (dd, J=3.6, 5.4 Hz, 1H), 6.89 (d, J=8.4 Hz, 1H), 4.11-4.05 (m, 4H), 3.08 (m, 1H), 2.66-2.62 (m, 3H), 2.60-2.30 (series of m, 2H), 1.94-1.22 (series of m, 12H)

Step-4:

A mixture of Intermediate 11 was hydrolyzed according to the procedure described in Example 6 Step 2 and gave 81 mg of the title compound 3-[(1-{4-[(5-phenylpentyl)oxy]-3-(2-thienyl)phenyl}ethyl)amino]cyclobutanecarboxylic acid $^1$H NMR (600 MHz, CD$_3$OD): δ 7.76 (d, J=2.4 Hz, 1H), 7.56 (dd, J=1.2, 4.2 Hz, 1H), 7.41 (dd, J=1.2, 5.4 Hz, 1H), 7.31 (dd, J=2.4, 9.0 Hz, 1H), 7.23 (t, J=7.8 Hz, 2H), 7.16 (d, J=7.8 Hz, 2H), 7.14-7.12 (m, 2H), 7.08 (dd, J=3.6, 5.4 Hz, 1H), 4.32 (q, J=7.2 Hz, 1H), 4.14 (t, J=6.0 Hz, 2H), 3.50 (t, J=7.8 Hz, 1H), 2.81-2.75 (m, 1H), 2.64 (t, J=7.8 Hz, 2H), 2.56-2.53 (m, 1H), 2.35-2.27 (m, 2H), 2.14-2.11 (m, 1H), 1.93-1.89 (m, 2H), 1.74-1.66 (m, 2H), 1.65 (d, J=6.6 Hz, 3H), 1.61-1.57 (m, 2H).

Example 8

Biological Data

Compounds were synthesized and tested for S1P1 activity using the GTP γ$^{35}$S binding assay. These compounds may be assessed for their ability to activate or block activation of the human S1P1 receptor in cells stably expressing the S1P1 receptor.

GTP γ$^{35}$S binding was measured in the medium containing (mM) HEPES 25, pH 7.4, MgCl$_2$ 10, NaCl 100, dithitothreitol 0.5, digitonin 0.003%, 0.2 nM GTP γ$^{35}$S, and 5 µg membrane protein in a volume of 150 µl. Test compounds were included in the concentration range from 0.08 to 5,000 nM unless indicated otherwise. Membranes were incubated with 100 µM 5'-adenylylimmidodiphosphate for 30 min, and subsequently with 10 µM GDP for 10 min on ice. Drug solutions and membrane were mixed, and then reactions were initiated by adding GTP γ$^{35}$S and continued for 30 min at 25° C. Reaction mixtures were filtered over Whatman GF/B filters under vacuum, and washed three times with 3 mL of ice-cold buffer (HEPES 25, pH7.4, MgCl$_2$ 10 and NaCl 100). Filters were dried and mixed with scintillant, and counted for $^{35}$S activity using a β-counter. Agonist-induced GTP γ$^{35}$S binding was obtained by subtracting that in the absence of agonist. Binding data were analyzed using a non-linear regression method. In case of antagonist assay, the reaction mixture contained 10 nM S1P in the presence of test antagonist at concentrations ranging from 0.08 to 5000 nM.

Table 3 shows activity potency: S1P1 receptor from GTP $\gamma^{35}$S: nM, (EC$_{50}$), % stimulation.

Activity Potency:

S1P1 receptor from GTP $\gamma^{35}$S: nM, (EC$_{50}$),

TABLE 3

| Compound number | IUPAC name | S1P1 EC$_{50}$ (nM) |
| --- | --- | --- |
| 16 | 1-{4-[(5-phenylpentyl)oxy]-3-(2-thienyl)benzyl}azetidine-3-carboxylic acid | 15 |
| 28 | 3-({4-[(5-phenylpentyl)oxy]-3-(2-thienyl)benzyl}amino)cyclobutanecarboxylic acid | 15 |
| 26 | 1-{4-[(5-phenylpentyl)thio]-3-(2-thienyl)benzyl}azetidine-3-carboxylic acid | 182 |
| 15 | 1-{3-cyclopent-1-en-1-yl-4-[(5-phenylpentyl)oxy]benzyl}azetidine-3-carboxylic acid | 13 |
| 25 | 1-{4-[(5-phenylpentyl)oxy]-3-(1H-pyrazol-1-yl)benzyl}azetidine-3-carboxylic acid | 22 |

Example 9

Lymphopenia Assay in Mice

Test drugs are prepared in a solution containing 3% (w/v) 2-hydroxy propyl β-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg. Blood samples are obtained by puncturing the submandibular skin with a Goldenrod animal lancet at 5, 24, 48, 72, and 96 hrs post drug application. Blood is collected into microvettes (SARSTEDT) containing EDTA tripotassium salt. Lymphocytes in blood samples are counted using a HEMAVET Multispecies Hematology System, HEMAVET HV950FS (Drew Scientific Inc.). (Hale, J. et al Bioorg. & Med. Chem. Lett. 14 (2004) 3351).

DETAILED DESCRIPTION OF DRAWINGS

A lymphopenia assay in mice; as previously described, was employed to measure the in vivo blood lymphocyte depletion after dosing with 1-{4-[(5-phenylpentyl)oxy]-3-(2-thienyl) benzyl}azetidine-3-carboxylic acid. This S1P1 agonist is useful for S1P-related diseases and exemplified by the lymphopenia in vivo response. Test drug, 1-{4-[(5-phenylpentyl) oxy]-3-(2-thienyl)benzyl}azetidine-3-carboxylic acid was prepared in a solution containing 3% (w/v) 2-hydroxy propyl ß-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg. Blood samples were obtained by puncturing the submandibular skin with a Goldenrod animal lancet at 5, 24, 48, and 72 hrs post drug application. Blood was collected into microvettes (SARSTEDT) containing EDTA tripotassium salt. Lymphocytes in blood samples were counted using a HEMAVET Multispecies Hematology System, HEMAVET HV950FS (Drew Scientific Inc.). Results are shown in the FIG. 1 that depicts lowered lymphocyte count after 5 hours (<1 number of lymphocytes 10$^3$/μL blood).

What is claimed is:

1. A compound having Formula I, its enantiomers, diastereoisomers, tautomers or a pharmaceutically acceptable salt thereof, Formula I wherein:
$R^1$ is C—$R^{11}$;
$R^2$ is optionally substituted aromatic heterocycle, optionally substituted non-aromatic heterocycle, optionally substituted cycloalkyl, optionally substituted cycloalkenyl or optionally substituted aryl;
$R^3$ is O or S;
$R^4$ is optionally substituted aryl;
$R^5$ is H, halogen or —O$C_{1-3}$ alkyl;
$R^6$ is H;
$R^7$ is H or $C_{1-6}$ alkyl;
$R^8$ is H;
$R^9$ is CH or N;
$R^{10}$ is carboxylic acid;
$R^{11}$ is H;
a is 0, 1, 2 or 3;
b is 0, 1, 2 or 3;
c is 1;
d is 0 or 1;
e is 0;
f is 1;
g is 0;
L is CHR$^{17}$ or O;
$R^{17}$ is H or $C_{1-3}$ alkyl; and
with the proviso that when $R^3$ is O or S and b is 0 or 1 then L is not O.

2. A compound according to claim 1, wherein:
$R^2$ is an optionally substituted 5-member aromatic heterocycle, or optionally substituted 5-member cycloalkenyl.

3. A compound according to claim 1, wherein:
$R^2$ is a cyclopentane, cyclopentene, pyrazolidine, pyrroline, pyrrolidine, imidazoline, pyrazoline, thiazoline, oxazoline, thiophene, dihydrothiophene, furan, dihydrofuran, pyrrole, pyrroline, pyrrolidine, oxazole, oxazoline, thiazole, imidazole, pyrazole, pyrazoline, isoxazole, isothiazole, tetrazole, oxadiazole, 1,2,5-oxadiazole, thiadiazole, 1,2,3-triazole, 1,2,4-triazole, imidazole, imidazoline, pyrrolidinone, pyrrol-2(3H)-one, imidazolidin-2-one, phenyl, 4-pyridine or 1,2,4-triazol-5(4H)-one.

4. A compound according to claim 1, wherein:
$R^9$ is CH; and
d is 1.

5. A compound according to claim 1, wherein:
$R^9$ is N; and
d is 0.

6. A compound according to claim 1, wherein:
$R^3$ is O.

7. A compound according to claim 1, wherein:
$R^3$ is S.

8. A compound according to claim 1, wherein:
L is CHR$^{17}$; and
$R^{17}$ is H or $C_{1-3}$ alkyl.

9. A compound according to claim 1, wherein:
L is O.

10. A compound according to claim 1 selected from:
- 1-{3-(3-furyl)-4-[(5-phenylpentyl)oxy]benzyl}azetidine-3-carboxylic acid;
- 1-{3-methoxy-4-[(5-phenylpentyl)oxy]-5-(2-thienyl)benzyl}azetidine-3-carboxylic acid;
- 1-{4-[(6-phenylhexyl)oxy]-3-(2-thienyl)benzyl}azetidine-3-carboxylic acid;
- 1-{4-[3-(benzyloxy)propoxy]-3-(2-thienyl)benzyl}azetidine-3-carboxylic acid;
- 1-[4-(2-biphenyl-4-ylethoxy)-3-(2-thienyl)benzyl]azetidine-3-carboxylic acid;
- 1-{3-chloro-4-[(5-phenylpentyl)oxy]-5-(2-thienyl)benzyl}azetidine-3-carboxylic acid;
- 1-{3-chloro-4-[(5-phenylpentyl)oxy]-5-(2-thienyl)benzyl}azetidine-3-carboxylic acid;
- 1-{4-[(3-methyl-5-phenylpentyl)oxy]-3-(2-thienyl)benzyl}azetidine-3-carboxylic acid;
- 1-{3-(5-methyl-2-thienyl)-4-[(5-phenyl pentyl)oxy]benzyl}azetidine-3-carboxylic acid;
- 1-{3-(4-methyl-2-thienyl)-4-[(5-phenyl pentyl)oxy]benzyl}azetidine-3-carboxylic acid;
- 1-{3-(3-methyl-2-thienyl)-4-[(5-phenyl pentyl)oxy]benzyl}azetidine-3-carboxylic acid;
- 1-{4-[(5-phenylpentyl)oxy]-3-(1,3-thiazol-5-yl)benzyl}azetidine-3-carboxylic acid;
- 1-{4-[(5-phenylpentyl)oxy]-3-(1,3-thiazol-4-yl)benzyl}azetidine-3-carboxylic acid;
- 1-{3-cyclopent-1-en-1-yl-4-[(5-phenyl pentyl)oxy]benzyl}azetidine-3-carboxylic acid;
- 1-{4-[(5-phenylpentyl)oxy]-3-(2-thienyl)benzyl}azetidine-3-carboxylic acid;
- 1-{4-[(5-phenylpentyl)oxy]-3-(1H-pyrazol-5-yl)benzyl}azetidine-3-carboxylic acid;
- 1-{4-[(5-phenylpentyl)oxy]-3-(1H-pyrazol-4-yl)benzyl}azetidine-3-carboxylic acid;
- 1-{4-[(5-phenylpentyl)oxy]-3-pyridin-4-ylbenzyl}azetidine-3-carboxylic acid;
- 1-{4-[(5-phenylpentyl)oxy]-3-(3-thienyl)benzyl}azetidine-3-carboxylic acid;
- 1-({6-[(5-phenylpentyl)oxy]biphenyl-3-yl}methyl)azetidine-3-carboxylic acid;
- 1-{3-(2-furyl)-4-[(5-phenylpentyl)oxy]benzyl}azetidine-3-carboxylic acid;
- 1-{4-[(5-phenylpentyl)oxy]-3-(1,3-thiazol-2-yl)benzyl}azetidine-3-carboxylic acid;
- 1-{3-(1,3-oxazol-2-yl)-4-[(5-phenylpentyl)oxy]benzyl}azetidine-3-carboxylic acid;
- 1-{4-[(5-phenylpentyl)oxy]-3-(1H-pyrazol-1-yl)benzyl}azetidine-3-carboxylic acid;
- 1-{4-[(5-phenylpentyl)thio]-3-(2-thienyl)benzyl}azetidine-3-carboxylic acid;
- 1-{3-cyclopent-1-en-1-yl-4-[(5-phenylpentyl)thio]benzyl}azetidine-3-carboxylic acid;
- 3-({4-[(5-phenylpentyl)oxy]-3-(2-thienyl)benzyl}amino)cyclobutanecarboxylic acid;
- 3-[(1-{4-[(5-phenylpentyl)oxy]-3-(2-thienyl)phenyl}ethyl)amino]cyclobutanecarboxylic acid.

11. A compound according to claim 1 selected from:
- 1-{3-(3-furyl)-4-[(5-phenylpentyl)oxy]benzyl}azetidine-3-carboxylic acid;
- 1-{3-chloro-4-[(5-phenylpentyl)oxy]-5-(2-thienyl)benzyl}azetidine-3-carboxylic acid;
- 1-{4-[(5-phenylpentyl)oxy]-3-(1,3-thiazol-5-yl)benzyl}azetidine-3-carboxylic acid;
- 1-{4-[(5-phenylpentyl)oxy]-3-(1,3-thiazol-4-yl)benzyl}azetidine-3-carboxylic acid;
- 1-{3-cyclopent-1-en-1-yl-4-[(5-phenyl pentyl)oxy]benzyl}azetidine-3-carboxylic acid;
- 1-{4-[(5-phenylpentyl)oxy]-3-(2-thienyl)benzyl}azetidine-3-carboxylic acid;
- 1-{4-[(5-phenylpentyl)oxy]-3-(1H-pyrazol-5-yl)benzyl}azetidine-3-carboxylic acid;
- 1-{4-[(5-phenylpentyl)oxy]-3-(1H-pyrazol-4-yl)benzyl}azetidine-3-carboxylic acid;
- 1-{4-[(5-phenylpentyl)oxy]-3-(3-thienyl)benzyl}azetidine-3-carboxylic acid;
- 1-{3-(2-furyl)-4-[(5-phenylpentyl)oxy]benzyl}azetidine-3-carboxylic acid;
- 1-{4-[(5-phenylpentyl)oxy]-3-(1,3-thiazol-2-yl)benzyl}azetidine-3-carboxylic acid;
- 1-{3-(1,3-oxazol-2-yl)-4-[(5-phenylpentyl)oxy]benzyl}azetidine-3-carboxylic acid;
- 1-{4-[(5-phenylpentyl)oxy]-3-(1H-pyrazol-1-yl)benzyl}azetidine-3-carboxylic acid;
- 3-({4-[(5-phenylpentyl)oxy]-3-(2-thienyl)benzyl}amino)cyclobutanecarboxylic acid;
- 3-[(1-{4-[(5-phenylpentyl)oxy]-3-(2-thienyl)phenyl}ethyl)amino]cyclobutanecarboxylic acid.

12. A pharmaceutical composition comprising as active ingredient a therapeutically effective amount of a compound according to claim 1 and a pharmaceutically acceptable adjuvant, diluents or carrier.

13. A pharmaceutical composition according to claim 12 wherein the compound is selected from:
- 1-{3-(3-furyl)-4-[(5-phenylpentyl)oxy]benzyl}azetidine-3-carboxylic acid;
- 1-{3-methoxy-4-[(5-phenylpentyl)oxy]-5-(2-thienyl)benzyl}azetidine-3-carboxylic acid;
- 1-{4-[(6-phenylhexyl)oxy]-3-(2-thienyl)benzyl}azetidine-3-carboxylic acid;
- 1-{4-[3-(benzyloxy)propoxy]-3-(2-thienyl)benzyl}azetidine-3-carboxylic acid;
- 1-[4-(2-biphenyl-4-ylethoxy)-3-(2-thienyl)benzyl]azetidine-3-carboxylic acid;
- 1-{3-chloro-4-[(5-phenylpentyl)oxy]-5-(2-thienyl)benzyl}azetidine-3-carboxylic acid;
- 1-{3-chloro-4-[(5-phenylpentyl)oxy]-5-(2-thienyl)benzyl}azetidine-3-carboxylic acid;
- 1-{4-[(3-methyl-5-phenylpentyl)oxy]-5-(2-thienyl)benzyl}azetidine-3-carboxylic acid;
- 1-{3-(5-methyl-2-thienyl)-4-[(5-phenyl pentyl)oxy]benzyl}azetidine-3-carboxylic acid;
- 1-{3-(4-methyl-2-thienyl)-4-[(5-phenyl pentyl)oxy]benzyl}azetidine-3-carboxylic acid;
- 1-{3-(3-methyl-2-thienyl)-4-[(5-phenyl pentyl)oxy]benzyl}azetidine-3-carboxylic acid;
- 1-{4-[(5-phenylpentyl)oxy]-3-(1,3-thiazol-5-yl)benzyl}azetidine-3-carboxylic acid;
- 1-{4-[(5-phenylpentyl)oxy]-3-(1,3-thiazol-4-yl)benzyl}azetidine-3-carboxylic acid;
- 1-{3-cyclopent-1-en-1-yl-4-[(5-phenylpentyl)oxy]benzyl}azetidine-3-carboxylic acid;
- 1-{4-[(5-phenylpentyl)oxy]-3-(2-thienyl)benzyl}azetidine-3-carboxylic acid;
- 1-{4-[(5-phenylpentyl)oxy]-3-(1H-pyrazol-5-yl)benzyl}azetidine-3-carboxylic acid;
- 1-{4-[(5-phenylpentyl)oxy]-3-(1H-pyrazol-4-yl)benzyl}azetidine-3-carboxylic acid;
- 1-{4-[(5-phenylpentyl)oxy]-3-pyridin-4-ylbenzyl}azetidine-3-carboxylic acid;
- 1-{4-[(5-phenylpentyl)oxy]-3-(3-thienyl)benzyl}azetidine-3-carboxylic acid;
- 1-({6-[(5-phenylpentyl)oxy]biphenyl-3-yl}methyl)azetidine-3-carboxylic acid;
- 1-{3-(2-furyl)-4-[(5-phenylpentyl)oxy]benzyl}azetidine-3-carboxylic acid;
- 1-{4-[(5-phenylpentyl)oxy]-3-(1,3-thiazol-2-yl)benzyl}azetidine-3-carboxylic acid;
- 1-{3-(1,3-oxazol-2-yl)-4-[(5-phenylpentyl)oxy]benzyl}azetidine-3-carboxylic acid;
- 1-{4-[(5-phenylpentyl)oxy]-3-(1H-pyrazol-1-yl)benzyl}azetidine-3-carboxylic acid;
- 1-{4-[(5-phenylpentyl)thio]-3-(2-thienyl)benzyl}azetidine-3-carboxylic acid;

1-{3-cyclopent-1-en-1-yl-4-[(5-phenylpentyl)thio]
benzyl}azetidine-3-carboxylic acid;

3-({4-[(5-phenylpentyl)oxy]-3-(2-thienyl)benzyl}amino)
cyclobutanecarboxylic acid;

3-[(1-{4-[(5-phenylpentyl)oxy]-3-(2-thienyl)
phenyl}ethyl)amino]cyclobutanecarboxylic acid.

14. A method of treating a disorder associated with sphingosine-1-phosphate (S1P) receptor modulation, wherein the disorder associated with sphingosine-1-phosphate (S1P) receptor modulation is rheumatoid arthritis, Crohn's disease, Graves' disease, inflammatory bowel disease, multiple sclerosis, Myasthenia gravis, Psoriasis, ulcerative colitis, antoimmune uveitis, renal ischemia, renal perfusion injury, contact hypersensitivity, atopic dermatitis or organ transplantation, which comprises administering to a mammal in need thereof, a pharmaceutical composition comprising a therapeutically effective amount of at least one compound of Formula I

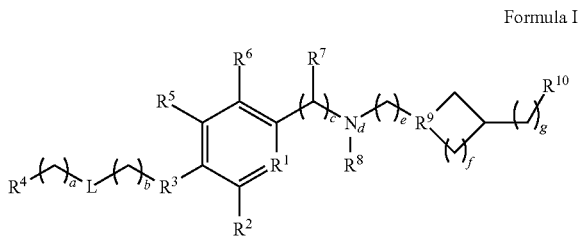

Formula I wherein:
$R^1$ is C—$R^{11}$;
$R^2$ is optionally substituted aromatic heterocycle, optionally substituted non-aromatic heterocycle, optionally substituted cycloalkyl, optionally substituted cycloalkenyl or optionally substituted aryl;
$R^3$ is O or;
$R^4$ is optionally substituted aryl;
$R^5$ is H, halogen or —$OC_{1-3}$ alkyl;
$R^6$ is H;
$R^7$ is H or $C_{1-6}$ alkyl;
$R^8$ is H;
$R^9$ is CH or N;
$R^{10}$ is carboxylic acid;
$R^{11}$ is H;
a is 0, 1, 2 or 3;
b is 0, 1, 2 or 3;
c is 1;
d is 0 or 1;
e is 0;
f is 1;
g is 0;
L is $CHR^{17}$ or O;
$R^{17}$ is H or $C_{1-3}$ alkyl and
with the proviso that when $R^3$ is O or S and b is 0 or 1 then L is not O.

15. The method of claim 14 wherein the mammal is a human.

16. A compound which is:
1-{4-[3-(4-isobutylphenyl)propoxy]-3-(2-thienyl)
benzyl}azetidine-3-carboxylic acid.

* * * * *

UNITED STATES PATENT AND TRADEMARK OFFICE
CERTIFICATE OF CORRECTION

PATENT NO. : 8,653,062 B2
APPLICATION NO. : 12/951317
DATED : February 18, 2014
INVENTOR(S) : Phong X. Nguyen et al.

Page 1 of 2

It is certified that error appears in the above-identified patent and that said Letters Patent is hereby corrected as shown below:

On the title page, item (56), under "Other Publications", in column 2, line 3, delete "Agonlsts"," and insert -- Agonists", --, therefor.

In the Specification

In column 4, line 41, after "alkyl" insert -- . --.

In column 7, line 47, delete "provision" and insert -- proviso --, therefor.

In column 7, line 58, delete "$R^5$" and insert -- $R^8$ --, therefor.

In column 8, line 13, delete "$R^5$" and insert -- $R^8$ --, therefor.

In column 10, line 27, delete "Chemica" and insert -- Chimica --, therefor.

In column 11, line 9, delete "antoimmune" and insert -- autoimmune --, therefor.

In column 11, line 10, delete "dermititis," and insert -- dermatitis, --, therefor.

In column 11, lines 56-57, delete "antoimmune" and insert -- autoimmune --, therefor.

In column 11, line 58, delete "dermititis," and insert -- dermatitis, --, therefor.

In column 15, lines 2-15, delete " 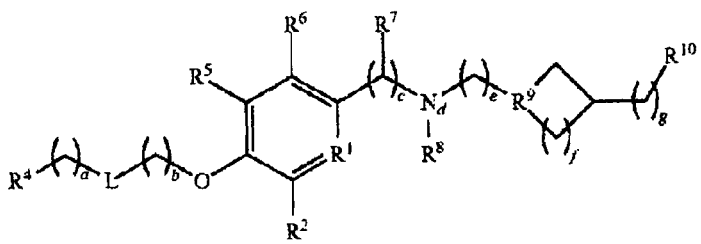 " and

Signed and Sealed this
First Day of July, 2014

Michelle K. Lee
*Deputy Director of the United States Patent and Trademark Office* insert -- 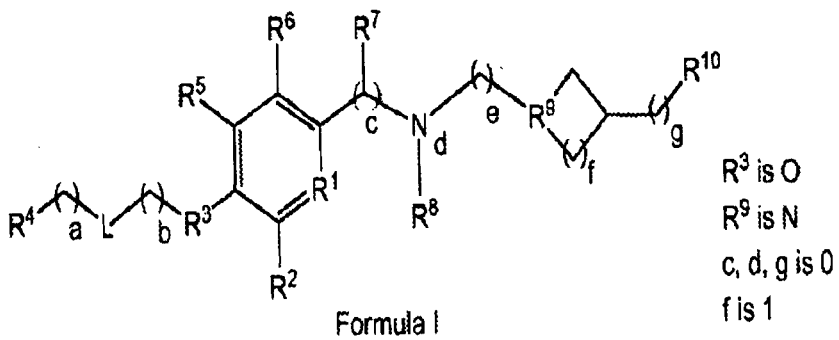 --, therefor.

In column 17, line 11, delete "R₇MgBr" and insert -- $R^7MgBr$ --, therefor.

In column 18, line 4, delete "diasteroisomeric" and insert -- diastereoisomeric --, therefor.

In column 19, lines 22-23, delete "benzldehyde" and insert -- benzaldehyde --, therefor.

In column 27, line 4, delete "oxazale" and insert -- oxazole --, therefor.

In column 27, line 58, delete "Na₂S 9H₂O" and insert -- $Na_2S \cdot 9H_2O$ --, therefor.

In column 29, line 52, delete "ove" and insert -- over --, therefor.

In column 30, line 3, after "387.19" and insert -- . --.

In column 30, line 25, after "12H)" and insert -- . --.

In column 30, line 30, after "acid" insert -- . --.

In column 30, lines 51-52, delete "dithitothreitol" and insert -- dithiothreitol --, therefor.

In column 30, line 56, delete "adenylylimmidodiphosphate" and insert -- adenylylimidodiphosphate --, therefor.

In the Claims

In column 35, lines 12-13, in claim 14, delete "antoimmune" and insert -- autoimmune --, therefor.